(12) United States Patent
Harston et al.

(10) Patent No.: US 10,512,261 B2
(45) Date of Patent: Dec. 24, 2019

(54) CONTAINERS FOR LIQUID NITROGEN STORAGE OF SEMEN STRAWS

(71) Applicant: Tokitae LLC, Bellevue, WA (US)

(72) Inventors: Stephen Paul Harston, Bothell, WA (US); Daniel Howard Lieberman, Issaquah, WA (US); Damian Madan, Issaquah, WA (US); Elizabeth Jane McClure, Seattle, WA (US); James Andrew Roecker, Bellevue, WA (US); Shannon Weise Stone, Redmond, WA (US)

(73) Assignee: Tokitae LLC, Bellevue, WA (US)

( * ) Notice: Subject to any disclaimer, the term of this patent is extended or adjusted under 35 U.S.C. 154(b) by 0 days.

(21) Appl. No.: 15/904,875

(22) Filed: Feb. 26, 2018

(65) Prior Publication Data

US 2018/0184645 A1    Jul. 5, 2018

Related U.S. Application Data

(63) Continuation-in-part of application No. 15/015,273, filed on Feb. 4, 2016, now abandoned.

(60) Provisional application No. 62/244,866, filed on Oct. 22, 2015, provisional application No. 62/169,719, filed on Jun. 2, 2015.

(51) Int. Cl.
*A61D 19/02* (2006.01)
*A01N 1/02* (2006.01)

(52) U.S. Cl.
CPC ......... *A01N 1/0273* (2013.01); *A01N 1/0268* (2013.01); *A61D 19/022* (2013.01); *A61D 19/024* (2013.01)

(58) Field of Classification Search
CPC .. A01N 1/0263; A01N 1/0273; A01N 1/0268; A01N 19/022; A01N 19/024; A61J 1/165; B01L 2300/0609; B01L 2300/1883; B01L 2300/1894; F17C 3/085; F25D 2303/0831; F25D 2303/0832; G01N 1/42; A61D 19/025; A61D 19/024; A61D 19/022

See application file for complete search history.

(56) References Cited

U.S. PATENT DOCUMENTS

| | | | |
|---|---|---|---|
| 3,108,840 | A | 10/1963 | Conrad et al. |
| 4,481,779 | A | 11/1984 | Barthel |
| 4,790,141 | A | 12/1988 | Glascock |
| 5,024,865 | A | 6/1991 | Insley |
| 5,419,143 | A | 5/1995 | Leonard et al. |
| 6,119,465 | A | 9/2000 | Mullens et al. |
| 6,467,642 | B2 | 10/2002 | Mullens et al. |
| 6,701,743 | B1 | 3/2004 | Durst et al. |

(Continued)

OTHER PUBLICATIONS

Rodriguez-Martinez, H.; "Can We Increase the Estimative Value of Semen Assessment?"; Reprod Dom Anim; 2006; pp. 2-10; vol. 41, Suppl. 2; Blackwell Verlag.

(Continued)

*Primary Examiner* — Mollie Impink

(57) ABSTRACT

Designs of improved canisters for animal semen straw storage in Dewars with cryogenic liquid are described. In some embodiments, the canisters include a layer of cryogen-absorbent material and an inner layer of thermally conductive material including apertures oriented and positioned to direct cryogen vapor into the interior of the container.

18 Claims, 14 Drawing Sheets

(56) References Cited

U.S. PATENT DOCUMENTS

| | | | |
|---|---|---|---|
| 7,299,650 | B1 | 11/2007 | Romanos et al. |
| 8,181,813 | B2* | 5/2012 | Cognard .................. A01N 1/02 220/23.83 |
| 8,956,855 | B2 | 2/2015 | Cognard et al. |
| 2005/0066682 | A1 | 3/2005 | Anthony |
| 2011/0022532 | A1 | 1/2011 | Kriss |
| 2011/0056902 | A1 | 3/2011 | Cognard |
| 2013/0091890 | A1 | 4/2013 | Schryver et al. |
| 2013/0105503 | A1 | 5/2013 | Cognard |
| 2013/0156659 | A1 | 6/2013 | Abrescia et al. |
| 2013/0232998 | A1 | 9/2013 | Ward et al. |
| 2013/0263622 | A1 | 10/2013 | Mullen et al. |

OTHER PUBLICATIONS

Rodriguez-Martinez, H.; "Laboratory Semen Assessment and Prediction of Fertility: still Utopia?"; Reprod Dom Anim; 2003; pp. 312-318; vol. 38; Blackwell Verlag, Berlin.

Sansiena et al.; "Implications of storage and handling conditions on glass transition and potential devitrification of oocytes and embryos"; Theriogenology; Aug. 2014; pp. 373-378; vol. 82, No. 3; Elsevier Inc.

Stroud, Brad; "Consequences of Mishandling Frozen Semen and Embryos"; Proceedings, Applied Reproductive Strategies in Beef Cattle; Dec. 3-4, 2012; pp. 191-204.

Walters et al.: "The history of sperm cryopreservation" Sperm Banking: Theory and Practice; pp. 1-10; Cambridge University Press.

Woldu et al.; "Factors affecting conception rate in artificially inseminated cattle under farmers condition in Ethiopia"; Journal of Cell and Animal Biology; Dec. 30, 2011; pp. 334-338; vol. 5, No. 16; Academic journals.

Lieberman et al.; "Maintaining semen quality by improving cold chain equipment used in cattle artificial insemination"; Scientific Reports; Jun. 17, 2016; pp. 1-9.

PCT International Search Report; International App. No. PCT/US2019/019358; dated Jun. 10, 2019; pp. 1-3.

CT Cryogenics; CT-3D Dry Vapor Shipper Semen Tank; product information; bearing a date of May 13, 2015; pp. 1-6.

Desta et al.; "Analyses of Dairy Cattle Breeding Practices in Selected Areas of Ethiopia"; Dissertation; Jul. 25, 2002; 175 pages.

Esteves et al.; "Evaluation of Acrosomal Status and Sperm Viability in Fresh and Cryopreserved Specimens by the Use of Fluorescent Peanut Agglutinin Lectin in conjunction with Hypo-osmotic Swelling Test"; International Braz J Urol; May-Jun. 2007; pp. 364-376; vol. 33. No. 3.

Holt,W. V.; "Basic aspects of frozen storage of semen"; Animal Reproduction Science; Aug. 2000; pp. 3-22; vol. 62; Elsevier Science B.V.

Hubel et al.; "Storage of Human Biospecimens: Selection of the Optimal Storage Temperature"; Biopreservation and BioBanking; 2014; pp. 165-175; vol. 12; No. 3; Mary Ann Liebert, Inc.

Ikawa et al.; "Fertilization: a sperm's journey to and interaction with the oocyte"; The Journal of Clinical Investigation; Apr. 2010; pp. 984-994; vol. 120; No. 4.

Kahi et al.; "Biotechnology in livestock production: Overview of possibilities for Africa"; African Journal of Biotechnology; Dec. 29, 2008; pp. 4984-4991; vol. 7, No. 25; pp. 4984-4991; Academic Journals.

Kivaria et al.; "Prospects and Constraints of Smallholder Dairy Husbandry in Dar es Salaam Region, Tanzania"; Outlook on Agriculture; Chapter 9; 2006; pp. 209-215; vol. 35, No. 3.

Lybaert et al.; "Improved methodology for the detection and quantification of the acrosome reaction in mouse spermatozoa"; Histology and Histopathology; 2009; pp. 999-1007; vol. 24.

Makoni et al.; "White Gold—Opportunities for Dairy Sector Development Collaboration in East Africa"; Technical Report; Jul. 2014; 208 pages.

Marle-Koster et al.; Current and Future Reproductive Technologies and World Food Production, in Current and Future Reproductive Technologies and World Food Production; bibliographic information (4 pages); Preface (2 pages); TOC(2 pages); pp. 199-211; Springer-Verlag New York.

Partyka et al.; "Methods of Assessment of Cryopreserved Semen"; 2012; Current Frontiers in Cryobiology; Prof. Igor Katkov (Ed.), ISBN: 978-953-51-0191-8, InTech; available from: http//www.intechooeb.com/books/current-frontiers-in-cryobiology/methods-ofassessment-of-cryopreserved-semen; pp. 547-575.

Pickett, B. W.; "Factors Affecting the Utilization of Frozen Bovine Semen for Maximum Reproductive Efficiency"; A. I. Digest; Feb. 1971; 16 pages; vol. XIX, No. 2.

Pickett et al.; "Influence of Seminal Additives and Packaging Systems on Fertility of Frozen Bovine Spermatozoa"; J Anim Sci; 1978; pp. 12-47; vol. 47.

Polge et al.; "Fertilizing Capacity of Bull Spermatozoa after Freezing at-79° C."; Nature; Apr. 12, 1952; pp. 626-627; vol. 169, No. 4302; Nature Publishing Group.

Rodriguez et al.; "Effect of Rates of Freezing, Thawing and Level of Glycerol on the Survival of Bovine Spermatozoa in Straws"; Journal of Animal Science; 1975; pp. 129-136; vol. 41, No. 1.

PCT International Search Report; International App. No. PCT/US2016/035160; dated Sep. 7, 2016; pp. 1-4.

Alejandrino et al.; "Constraints on dairy cattle productivity at the smallholder level in the Philippines"; Preventative Veterinary Medicine; 1999; pp. 167-178; vol. 38; Elsevier Science B.V.

Bailey et al.; "Semen Cryopreservation in Domestic Animals: A Damaging and Capacitating Phenomenon"; Journal of Andrology; Jan./Feb. 2000; pp. 1-7; vol. 21, No. 1; American Society of Andrology.

Ball et al.; "Factors Affecting Successful In Vitro Fertilization of Bovine Follicular Oocvtes"; Biology of Reproduction; Nov. 3, 1983; pp. 717-725; vol. 28.

Barua, Proloy; "Analytical Documentation of the Artificial Insemination Programme of BRAC"; BRAC Research Report; Apr. 2006; 20 pgs.

Berndtson et al.; "Procedures for Field Handling of Bovine Semen in Plastic Straws"; Animal Reproduction Laboratory; Department of Physiology and Biophysics; pp. 51-60; printed on Jan. 28, 2016.

Bratton et al.; "Preliminary Fertility Results with Frozen Bovine Spermatozoa"; Journal of Dairy Science; Jan. 1955; pp. 40-46; vol. 38, Issue 1; Elsevier Inc.

Celeghini et al.; "Practical Techniques for Bovine Sperm Simultaneous Fluorimetric Assessment of Plasma, Acrosomal and Mitochondrial Membranes"; Reprod Dom Anim; 2007; pp. 479-488; vol. 42; Blackwell Verlag.

* cited by examiner

FIG. 2A.
FIG. 2 B.
Fig. 2C.
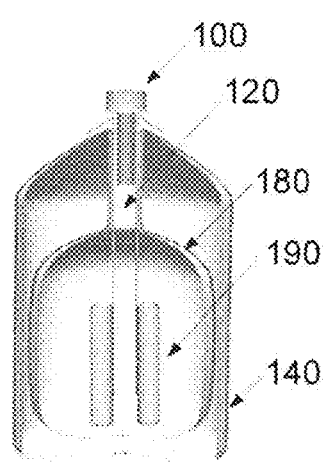
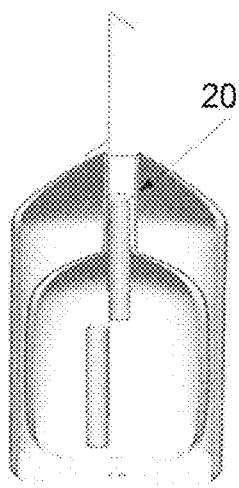
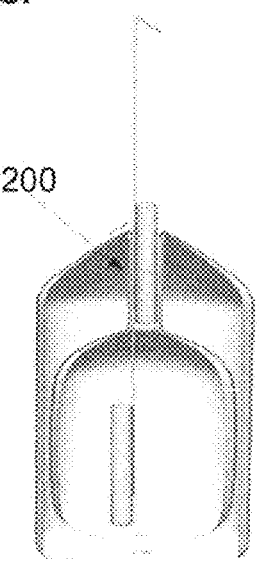

CONTAINERS FOR LIQUID NITROGEN STORAGE OF SEMEN STRAWS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 15/015,273, entitled CONTAINERS FOR LIQUID NITROGEN STORAGE OF SEMEN STRAWS, naming Stephen Paul Harston, Daniel Howard Lieberman, Damian Madan, Elizabeth Jane McClure, James Andrew Roecker, and Shannon Weise Stone as inventors, filed 4 Feb. 2016, which is currently co-pending or is an application of which a currently co-pending application is entitled to the benefit of the filing date.

The present application claims benefit of priority of U.S. Provisional Patent Application No. 62/169,719, entitled SIMPLE TECHNOLOGY TO IMPROVE ARTIFICIAL INSEMINATION OF DAIRY CATTLE: DESIGNS THAT MITIGATE POOR HANDLING PRACTICES IN THE DEVELOPING WORLD, naming Marie Connett, Stephen Harston, Daniel Lieberman, Damian Madan, Elizabeth McClure, Jon Porter and Jim Roecker as inventors, filed 2, Jun. 2015, which was filed within the twelve months preceding the filing date of the present application or is an application of which a currently co-pending priority application is entitled to the benefit of the filing date.

The present application claims benefit of priority of U.S. Provisional Patent Application No. 62/244,866, entitled MAINTAINING SEMEN QUALITY BY IMPROVING COLD CHAIN EQUIPMENT USED IN CATTLE ARTIFICIAL INSEMINATION, naming Stephen Harston, Daniel Lieberman, Damian Madan, and Elizabeth McClure as inventors, filed 22, Oct. 2015, which was filed within the twelve months preceding the filing date of the present application or is an application of which a currently co-pending priority application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In some embodiments, a canister for liquid cryogen storage includes: a cylindrical cup with a circular side wall and a bottom wall; a series of apertures in the circular side wall; and a flange affixed to an interior surface of the circular side wall at a position adjacent to the apertures.

In some embodiments, a canister for liquid cryogen storage includes: a cylindrical cup with a circular side wall and a bottom wall; and a layer of absorbent material affixed to the interior surface of the circular side wall, the absorbent material absorbent to a liquid cryogen.

In some embodiments, a canister for liquid cryogen storage includes: a cylindrical cup with a circular side wall and a bottom wall; and a solid mass of a size and shape to substantially fill the interior of the cylindrical cup, the solid mass including a plurality of cavities positioned vertically in the solid mass.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2A shows a cross section of a Dewar.
FIG. 2B illustrates recommended practices with a Dewar.
FIG. 2C depicts poor handling practices with a Dewar.

DETAILED DESCRIPTION

Figure 1:
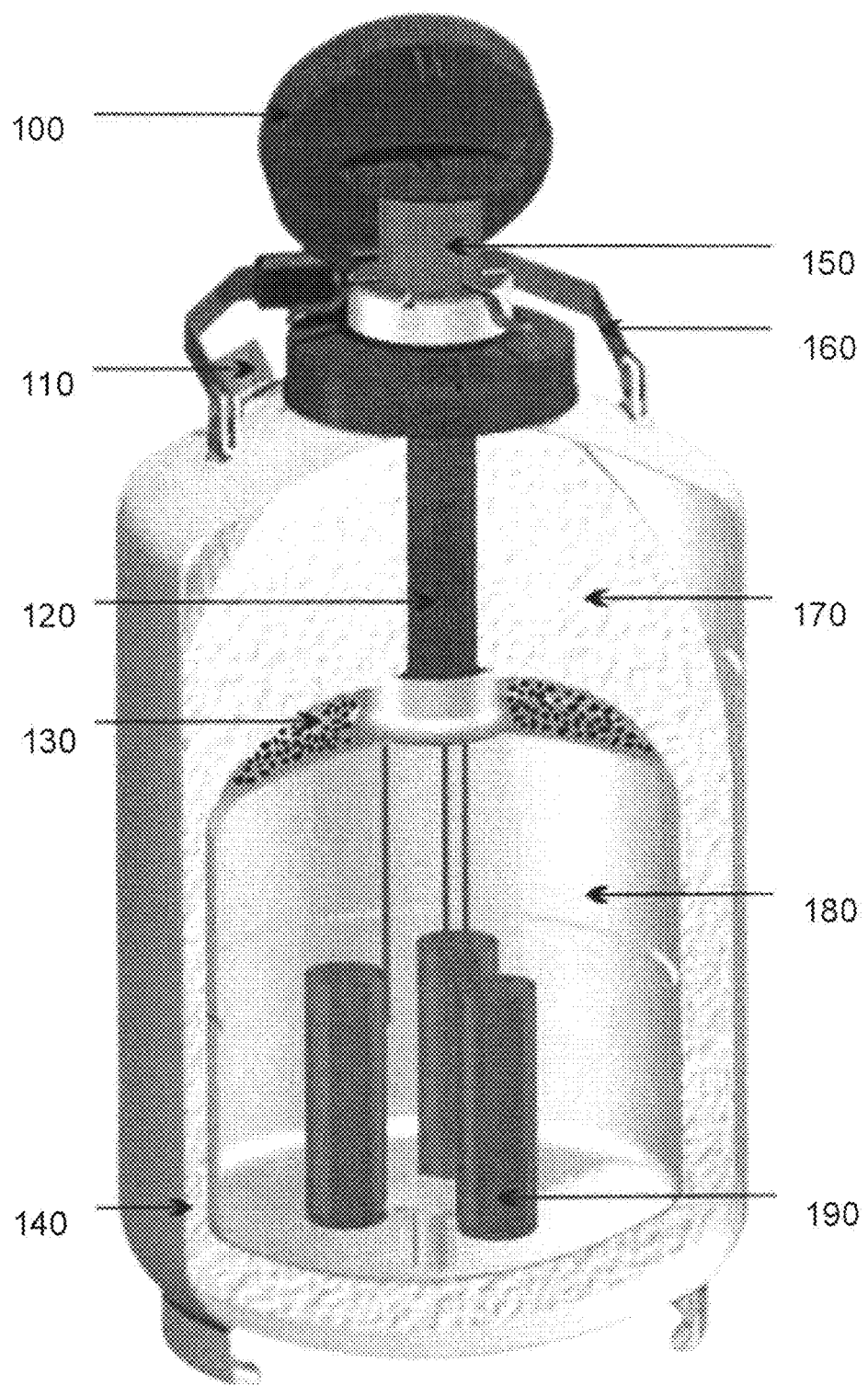
FIG. 1 depicts aspects of a Dewar.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Artificial insemination of dairy cattle is a common practice in the developing world that can improve farmer incomes and food security. Maintaining the fertilizing potential of frozen semen as it is manipulated, transported and stored is crucial to the success of this process. Described herein are technological improvements to protect semen from inadvertent thermal fluctuations that occur when poor handling practices are used with standard equipment. When frozen semen is subjected to poor handling practices using standard equipment, certain characteristics of semen biology associated with fertility are negatively affected. Herein is described several design improvements and results from thermal performance tests of several improved prototypes. Experiments have compared semen that has experienced poor handling practices in standard and improved equipment. These data suggest that an improved canister can better maintain the fertility of frozen semen when subjected to poor handling.

Over the last few centuries selective breeding has developed dairy cattle breeds that produce large quantities of milk. By contrast, indigenous cows in the developing world are far less productive (N. Makoni, T. Redda, J. van der Lee, R. Mwai, and A. van der Zijpp, "White gold—Opportunities for dairy sector development collaboration in East Africa," 2014 and A. K. Kahi and T. O. Rewe, "Biotechnology in livestock production: Overview of possibilities for Africa," African J. Biotechnol., Vol. 7, No. 25, pp. 4984-4991, 2008, which are each incorporated by reference). Recognizing this large discrepancy, many developing counties strive to improve milk yields—and therefore farmers' incomes and food security—by utilizing the genetics of nonendemic breeds. While traditional mating of imported cattle is used to generate both cross and full breeds, artificial insemination (AI) is the prevailing method used to accomplish this goal (E. van Marle-Köster and E. Webb, "Current and Future Reproductive Technologies and World Food Production," in Current and Future Reproductive Technologies and World Food Production SE—10, Vol. 752, G. C. Lamb and N. DiLorenzo, Eds. New York, N.Y.: Springer N.Y., 2014, pp. 199-211, which is incorporated by reference).

Perhaps the greatest breakthrough to impact the practice of AI came in the 1950s when glycerol was discovered to act as a cryoprotectant for dairy bull semen (R. W. Bratton, R. H. Foote, and J. C. Cruthers, "Preliminary Fertility Results with Frozen Bovine Spermatozoa," J. Dairy Sci., Vol. 38, No. 1, pp. 40-46, 1955 and C. Polge and L. E. A. Rowson, "Fertilizing capacity of bull spermatozoa after freezing at −79 C," Nature, Vol. 169, pp. 626-627, 1952, which are each incorporated by reference). This advance allowed for a much greater temporal, and therefore spatial, separation between semen collection and insemination. Now, semen is generally collected, packaged into standard-sized semen straws, and frozen at centralized facilities. The frozen semen is then shipped throughout the world in Dewars containing liquid nitrogen (LN).

Four variables affect whether AI will result in conception: heat detection, inseminator efficiency, fertility of the heifer, and the fertility of the semen (C. Polge and L. E. A. Rowson, "Fertilizing capacity of bull spermatozoa after freezing at −79 C," Nature, Vol. 169, pp. 626-627, 1952 and K. B. Desta, "Analyses of Dairy Cattle—Breeding Practices in Selected Areas of Ethiopia Dissertation," 2002, which are each incorporated by reference). Mammals are fertile only for a limited window of time during each reproductive cycle, so effectively determining that a heifer is in heat is vital for AI success. Similarly, the competency of an inseminator is important to properly deliver semen hygienically and on target. These first two variables are most effectively managed through proper AI technician training. Heifer fertility, the third variable influencing AI success, is affected by diseases such as mastitis, the length of the post-partum waiting period, and nutrition, and is shaped by heifer management throughout its life.

Semen fertility, the final variable in AI success, is most commonly affected by handling subsequent to semen packaging and freezing (B. W. Pickett, "Factors affecting the utilization of frozen bovine semen for maximum reproductive efficiency," A. I. Dig., Vol. 19, No. 2, p. 8, 1971 which is incorporated by reference). A vast amount of research has optimized the number of sperm packed per standard-sized straw, the additives that supplement semen, and the precise protocols used to properly freeze this mixture (E. M. Walters, J. D. Benson, E. J. Woods, and J. K. Critser, "The history of sperm cryopreservation," 2009 and W. V Holt, "Basic aspects of frozen storage of semen," Anim. Reprod. Sci., Vol. 62, No. 1-3, pp. 3-22, August 2000, which are each incorporated by reference). Once a lot of semen has been frozen into individual straws, bull stud ranches generally perform quality control assessments by assaying in vitro characteristics that are associated with fertilizing potential (H. Rodriguez,-Martinez, "Can We Increase the Estimative Value of Semen Assessment," Reproduction Domest. Anim., Vol. 41, pp. 2-10, 2006 and L. Z. Oliveira, F. M. Monteiro, E. Carla, and C. Celeghini, Success in Artificial Insemination—Quality of Semen and Diagnostics Employed, 2013, which are each incorporated by reference). Consequently, semen sold by most reputable bull stud ranches is generally highly fertile, and if stored properly in its original packaging in LN, will retain its fertilizing potential indefinitely (R. H. Foote, "The history of artificial insemination: Selected notes and notables," J. Anim Sci., Vol. 80, pp. 1-10, 2002, which is incorporated by reference).

However, subsequent improper handling by prematurely breaking the cold chain can dramatically decrease a semen straw's fertility. In order to prevent this thermally-induced semen damage, most developed world bovine inseminators are taught to never remove semen straws from LN for more than very brief periods, unless the straw is being thawed for immediate usage. Rules of thumb limit exposures to eight, five or even three seconds (B. Stroud, "Consequences of mishandling frozen semen and embryos," Proceedings, Appl. Reprod. Strateg. Beef Cattle, pp. 191-204, 2012, which is incorporated by reference). These rules are stressed during inseminator training because very short exposures to ambient temperatures can cause large temperature fluctuations within the straws (W. E. Berndtson, B. W. Pickett, C. D. Rugg, and F. Collins, "Procedures for Field Handling of Bovine Semen in Plastic Straws," pp. 51-60, 1973, which is incorporated by reference). While these fluctuations are often not large enough to thaw the straw's contents, they do cause cumulative and irreversible damage that negatively impacts the fertilizing potential of semen (W. V Holt, "Basic aspects of frozen storage of semen," Anim. Reprod. Sci., Vol. 62, No. 1-3, pp. 3-22, August 2000; B. Stroud, "Consequences of mishandling frozen semen and embryos," Proceedings, Appl. Reprod. Strateg. Beef Cattle, pp. 191-204, 2012; B. W. Pickett, W. E. Berndtson, and J. J. Sullivan, "Influence of seminal additives and packaging systems on fertility of frozen bovine spermatozoa," J. Anim. Sci., Vol. 47, Suppl 2. pp. 12-47, 1978; 0. Rodriguez, W. Berndtson, B. Ennen, and B. Pickett, "Effect of rates of freezing, thawing and level of glycerol on the survival of bovine spermatozoa in straws," J. Anim. Sci., pp. 129-136, 1975 and B. W. Pickett, "Factors Affecting the Utilization of Frozen Bovine Semen for Maximum Reproductive Efficiency," First N.A.A.B. Tech. Conf., p. 64, 1966, which are each incorporated by reference).

Much of the equipment used to store and categorize the standard-sized straws in a Dewar was designed to promote proper handling practices. The plastic goblets and cane assemblies used in Dewars with 20 liter or greater capacity were designed for semen straw storage and have been demonstrated to help improve protection from inadvertent exposure (W. E. Berndtson, B. W. Pickett, C. D. Rugg, and F. Collins, "Procedures for Field Handling of Bovine Semen in Plastic Straws," pp. 51-60, 1973, which is incorporated by reference). These larger Dewars, however, are used less frequently in developing countries where farms are typically much smaller, increasing the need for an AI technician to be mobile. In developing countries, smaller 3 L Dewars are most common as they are easily transported by motorcycle (P. Barua, "Analytical Documentation of the Artificial Insemination Programme of BRAC," BRAC Res. Rep., 2006, which is incorporated by reference). The smaller size of these Dewars does not allow the use of the canes. Consequently goblets are uncommon and semen straws are often placed directly in the canister.

A limited number of studies and a large amount of anecdotal evidence suggest that poor handling of frozen semen is a frequent occurrence. One study compared several morphological and motility characteristics in semen stored at operational farms and a facility where proper handling practices were tightly controlled. Semen stored at the farm showed significant damage, suggesting that proper handling guidelines were not followed (M. Pace, L. Peterson, G. VanDellen, E. Waterman, R. Robbins, and J. Sullivan, "Effect of field working storage upon quality of frozen bull spermatozoa packaged in 0.5 ml ampoules and 0.5 ml French straws," in American Society of Animal Science Annual Meeting, 1977, p. 194, which is incorporated by reference). A more recent study measured in vitro fertilization rates and showed that if post-thaw sperm microscopically diagnosed as poor quality—attributed by the author as largely due to routine poor handling practices—are removed, there is a 9% improvement in embryo fertilization (B. Stroud, "Consequences of mishandling frozen semen and embryos," Proceedings, Appl. Reprod. Strateg. Beef Cattle, pp. 191-204, 2012 and F. N. Schrick, F. M. Saxton, and B. K. Stroud, "Assessment of semen quality for predicting recovery of viable embryos of superovulated cattle," in Joint Cony Proc CETA/AETA, 2003, which are each incorporated by reference).

Proper technique dictates that canisters holding the semen straws be held below the frost line in the neck of the Dewars for limited amount of time during removal of straws. However, it has been demonstrated that sometimes canisters and their enclosed straws are raised well above the frost line in the Dewar neck or removed entirely from the Dewar neck.

FIG. 1 depicts a representative example of a commercially-available Dewar (e.g. YDS-3 3 L Dewar, Chart Industries, Garfield Heights, Ohio, and/or XTL3 3L Dewar, Taylor-Wharton Industries, Mobile Ala.). A locking cover 100 reversibly covers the top opening of the container. A cork 150 reversibly mates with the interior of the neck tube 120. A handle 160 is affixed to the exterior of the container. An evacuating nozzle 110 is positioned at the upper face of the container. The neck tube 120 provides a conduit between the outer shell 140 and the inner vessel 180. Multi-layer thermal insulation 170 is positioned between the outer shell 140 and the inner vessel 180 and surrounding the neck tube 120. Adsorbent material 130 is positioned at the upper surface of the inner vessel 180, the adsorbent material surrounding the neck tube 120. Multiple canisters 190 are positioned in the lower portion of the inner vessel 180. Each canister 190 includes a handle that projects upward and into the neck tube 120. The canisters are of a size and shape to hold standard-sezed semen straws during storage and transport within the Dewar.

Training is often less rigorous in the developing world, implying that handling-induced semen damage is likely an even greater problem in these areas. Indeed, the number of AI services per conception is generally higher in developing countries (E. van Marle-Köster and E. Webb, "Current and Future Reproductive Technologies and World Food Production," in Current and Future Reproductive Technologies and World Food Production SE—10, Vol. 752, G. C. Lamb and N. DiLorenzo, Eds. New York, N.Y.: Springer N.Y., 2014, pp. 199-211, which is incorporated by reference), and improper semen handling contributes to these differences (T. Woldu, "Factors affecting conception rate in artificially inseminated cattle under farmers condition in Ethiopia," J. Cell Anim. Biol., Vol. 5, No. 16, pp. 334-338, 2011, F. M. Kivaria, J. P. T. M. Noordhuizen, and A. M. Kapaga, "Prospects and constraints of smallholder dairy husbandry in the Dar es Salaam region, Tanzania," Outlook Agric., Vol. 35, No. 3, pp. 209-215, 2006 and A. L. Alejandrino, C. O. Asaad, B. Malabayabas, A. C. De Vera, M. S. Herrera, C. C. Deocaris, L. M. Ignacio, and L. P. Palo, "Constraints on dairy cattle productivity at the smallholder level in the Philippines," Prev. Vet. Med., Vol. 38, No. 2-3, pp. 167-178, 1999, which are each incorporated by reference).

FIGS. 2A, 2B and 2C depict aspects of handling of containers and their enclosed semen straws within a Dewar. FIG. 2A depicts a cross-section view of a Dewar including a cover 100 and a neck tube 120. The device is positioned for storage of the canisters containing semen straws within the storage region of the inner vessel 180. The neck tube 120 is affixed at its lower edge to an inner vessel 180. An outer shell 140 surrounds the inner vessel 180. Multiple storage canisters 190 are held within the inner vessel 180 for semen straw storage. During use, the inner vessel 180 would include a cryogen, such as liquid nitrogen (LN) immersing the semen straws within the canisters. FIG. 2B shows a cross-section view of the Dewar to illustrate recommended practices to access semen straws within a canister. The canister is brought up to the edge of the frost line 200 for access, but does not pass beyond the frost line 200. FIG. 2C depicts a cross-section view of a Dewar to illustrate common poor handling practices. The canister is elevated above the frost line 200 of the Dewar while semen straws are removed, exposing the straws to a potentially damaging temperature.

Generally multiple semen straws are stored within a canister. If poor handling practices are routinely used—such as each time an AI technician removes a straw for immediate usage—remaining straws within the inventory will experience multiple thermal exposures. It has been suggested that semen damage results when the bulk product temperature rises above $-130°$ C., the glass transition temperature of water, and then cools back down when re-introduced to the LN immersion (B. Stroud, "Consequences of mishandling frozen semen and embryos," Proceedings, Appl. Reprod. Strateg. Beef Cattle, pp. 191-204, 2012 and W. E. Berndtson, B. W. Pickett, C. D. Rugg, and F. Collins, "Procedures for Field Handling of Bovine Semen in Plastic Straws," pp. 51-60, 1976, which are each incorporated by reference).

In an effort to improve AI success rates in the developing world, inexpensive and easy to use technology has been developed that protects stored semen straws within canisters from thermal exposures, as described further below. Aspects of semen damage that occur when frozen straws are subjected to common poor handling practices were quantified. The design and thermal performance of multiple semen canister prototypes is described. Frozen semen stored in a standard and in improved canisters were subjected to repeated ambient temperature exposures. Subsequent analysis shows that semen stored in the improved canister possesses characteristics of more highly fertile semen.

Prototype Design and Testing

The canister found in most small portable Dewars used for AI consists of a cylindrical cup with a handle to allow manipulation inside a Dewar and to rest on a hook at the neck. A grate can be attached to the canister base to allow LN to flow out as it is raised.

Figure 3:
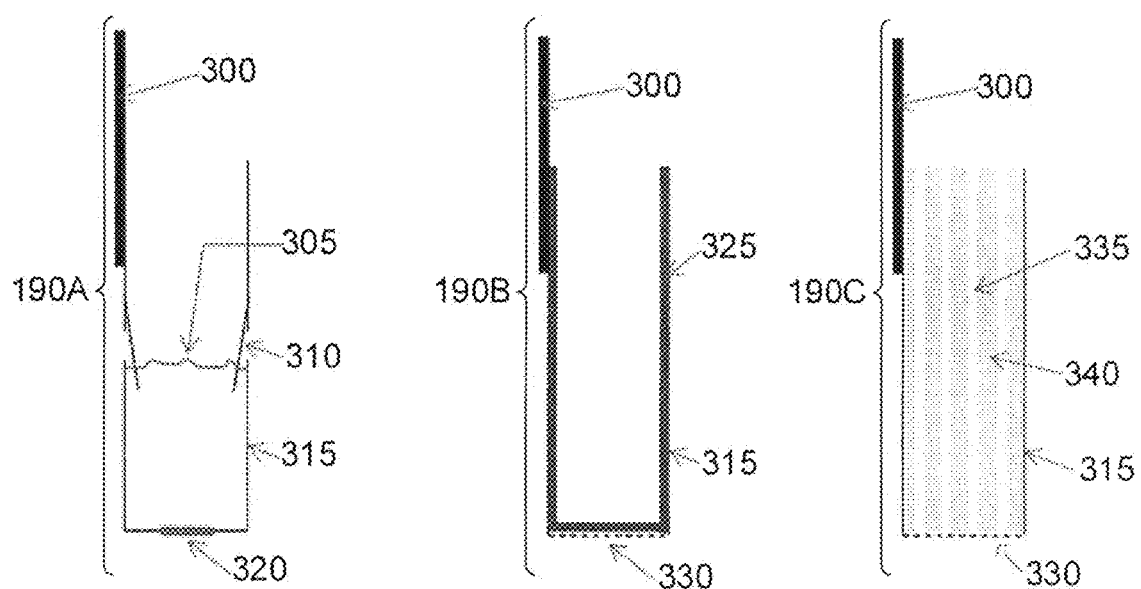
FIG. 3 is a schematic of three canister embodiments.

Multiple prototype canister designs were developed and evaluated, some of these are depicted in FIG. 3. FIG. 3 is a cross-section schematic of Prototype Design 1 190A (left), prototype Design 2 190B (center), and prototype Design 3 190C (right).

FIG. 3 shows prototype Design 1 190A to the left side of the Figure. The embodiment includes a handle 300 affixed to the canister wall 315. Design 1 190A is shown with a cryogen 305, such as liquid nitrogen, within the canister, while a vapor guard 310 maintains the liquid nitrogen 305 within the canister. A porous or permeable membrane 320 is positioned at the lower surface of the canister.

The prototyped canister Design 1 190A retains a liquid cryogen, such as LN, during regular operation resulting in lower semen straw temperatures during poor handling practices. In the embodiment illustrated in FIG. 3, Design 1 190A includes a sealed canister base to retain LN when the canister is raised. The design features of Design 1 also include drain holes, drilled along the circumference, anywhere from one quarter to halfway up from the bottom of the canister, the drain holes spaced to control the level of liquid cryogen 305 within the canister. The holes are positioned to allow the canister to fill when the liquid cryogen 305 level in the Dewar is below the top of the canister. With this design, a canister of Design 1 190A will gradually sink when inserted into the Dewar as the cryogen fills the canister.

Features of Design 1 can include a vapor guard 310 that is fixed to the inside wall of the canister along the circumference to cover the drain holes and extend below the cryogen liquid level. The function of the vapor guard skirt structure is to minimize cryogen vapor from flowing out of the holes when a canister of Design 1 is withdrawn from the Dewar during use.

In some embodiments, Design 1 includes a base fitted with a permeable membrane 320 designed to allow a liquid cryogen to slowly fill over several hours while restricting any meaningful amount of the liquid cryogen from exiting during a straw extraction event lasting up to a few minutes. For example, in some embodiments the permeable membrane includes a sintered metal. The use of such a membrane will extend also the effectiveness of this device when the liquid cryogen level in the Dewar drops below the elevation of the drain holes during storage or transport.

FIG. 3 depicts prototype Design 2 190B in the center of the Figure. The embodiment includes a handle 300 affixed to the canister wall 315. A liquid cryogen absorbent material 325 is positioned adjacent to the inner surface of the canister wall 315. For example, in some embodiments the absorbent material is absorbent of liquid nitrogen. Some embodiments include a thermally conductive liner positioned adjacent to the surface of the liquid cryogen absorbent material within the interior of the canister. The thermally conductive liner is fabricated from a material with thermal conduction properties sufficient to equalize the temperature between the top and the bottom of the container interior wall to match the cryogen within the container quickly, within a few seconds. Such themal equalization will assist in protection of stored semen straws from temperature shifts when the canister is pulled above the frost line of a Dewar for straw removal. A thermally conductive liner includes apertures positioned and agled to direct cryogen vapor towards the interior of the canister and surround any enclosed semen straws within the center. The cryogen vapor assists in maintaining the temperature of the stored semen straws at near cryogen temperature during a period of time when the canister is raised above the frost line. The embodiment 190B includes a grated base 330 at the lower face of the canister.

The canister wall and base are lined with an absorbent material positioned to absorb liquid cryogen and provide additional insulation (see FIG. 3). The design permits the liquid cryogen to drain from a grated canister base as it is raised. Some embodiments include a LN absorbent material. Some embodiments include a LN absorbent material that includes a flexible aerogel. Some embodiments include a LN absorbent material that includes a woven fiberglass material. The LN absorbent material provides thermal isolation from the environment and blankets straws with cold nitrogen vapor as the liquid vaporizes. The thickness of the material is designed to store sufficient liquid cryogen for a short exposure up to several minutes. In some embodiments, the absorbent material is between approximately 2 mm and approximately 7 mm in thickness. The design including liquid cryogen absorbent material at the canister base allows liquid to fill and drain during use.

FIG. 3 illustrates prototype Design 3 190C at the right of the Figure. The embodiment includes a handle 300 affixed to the canister wall 315. The embodiment 190C includes a grated base 330 at the lower face of the canister. The embodiment 190C includes a solid mass 340 positioned within the canister. A series of apertures 335 are positioned substantially vertically within the solid mass 340. The apertures 335 include an opening at the top face of the solid mass 340. The apertures 335 project vertically from the top face of the solid mass 340 into the solid mass 340 for a depth at least as long as a semen straw expected to be stored within the canister 315.

The canister is designed to include solid mass with a system of holes along its length to insert several straws (see FIG. 3). The holes form apertures oriented along the long axis of the Design 3 canister. The holes can be designed to sort straws from different bulls. For example, in some embodiments the holes are sized, shaped, and positioned to store semen straws in different sections that can be easily identified by a user based on one or more of these factors.

The solid mass can be fabricated, for example, from a heat-conductive material, such as a thermally-conductive metal. In some embodiments, the solid mass of the canister is fabricated from aluminum. In some embodiments, the solid mass of the canister is fabricated from copper. In some embodiments, the solid mass of the canister is fabricated from stainless steel. The solid construction is designed to provide additional thermal mass relative to a standard canister, thus slowing the temperature rise during an exposure to remain below −130 degrees C.

We conceived of approaches to improve the canister design to decrease thermal fluctuations within semen straws when the canister is removed from the Dewar. Prototype versions of some designs are depicted in FIGS. 4B, 4C and 4D.

FIG. 4 depicts additional aspects of canisters for storage of semen straws within a Dewar. FIG. 4A, 4B, 4C, 4D depicts prototype schematics in cross-section. FIGS. 4B, 4C and 4D depict additional aspects of Design 1, Design 2 and Design 3 as described above.

Figure 4A:
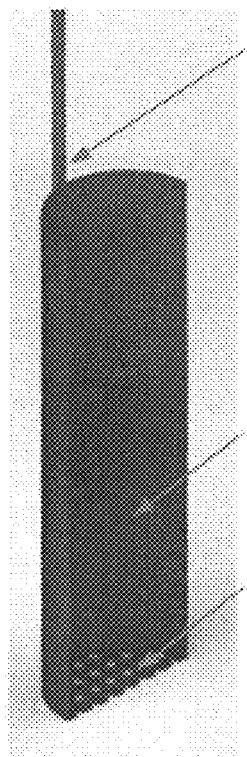
FIG. 4A is a cross-section depiction of a canister.

FIG. 4A shows a depiction of a canister found in many small portable Dewars. FIG. 4A depicts a representative example of the standard canister design in a cross-section view. The cylindrical cup 315 that holds semen straws is attached to a handle 300 that allows manipulation inside a Dewar and to rest on a hook at the neck. A grate 330 or drain holes are incorporated into the canister base to allow liquid cryogen to empty as it is raised. The canisters found in most small portable Dewars used for AI consist of a cylindrical cup with a handle to allow manipulation inside a Dewar and to rest on a hook at the neck. A grate or drain holes 330 are incorporated into the canister base to allow liquid cryogen to flow out as it is raised. A handle 300 is affixed to a top edge of the canister wall 315. The bottom of the canister includes a grated base 330.

Figure 4B:
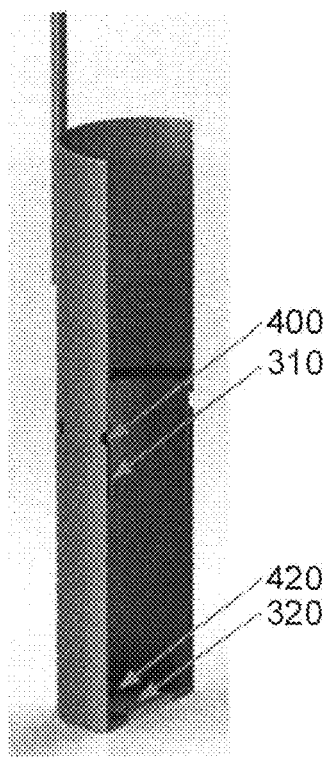
FIG. 4B is a cross-section depiction of a canister.
Figure 4C:
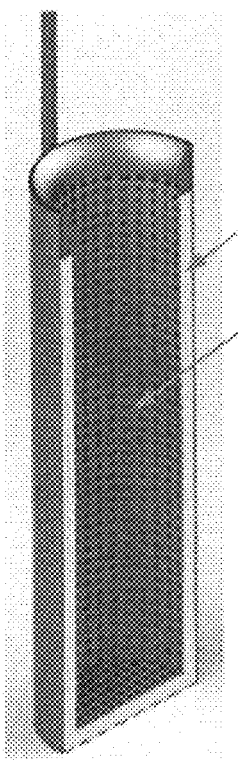
FIG. 4C is a cross-section depiction of a canister.
Figure 4D:
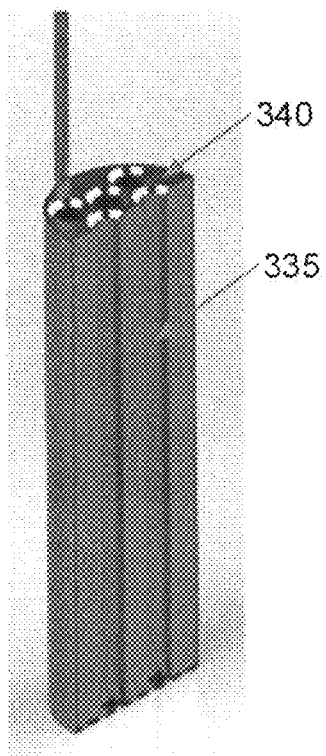
FIG. 4D is a cross-section depiction of a canister.

FIG. 4B depicts aspects of Design 1. When the canister is in the resting position in the Dewar, liquid cryogen enters the canister through drain holes 400. The drain holes 400 are positioned above the base of the container at a position approximately one third to one half of the length of the container. When the canister is raised, cold cryogen vapor (e.g. cold nitrogen vapor) fills the top half of the canister as liquid cryogen maintained at the base of the canister boils. A vapor guard 310 is included to minimize vapor exit via the drain holes. The vapor guard 310 is formed as a skirt or flap structure affixed at its upper edge to a position above the drain holes 400, with the lower edge of the vapor guard 310 extending below the level of the drain holes 400. In some embodiments, the lower edge of the vapor guard fully covers one or more of the drain holes. In some embodiments, the lower edge of the vapor guard partially covers one or more of the drain holes. Depending on the embodiment, a vapor guard can be fabricated from a thin metal sheet, for example fabricated from a stainless steel or aluminum sheet. In some embodiments, the vapor guard is fabricated from the same material as the canister walls.

The grate at the base of the canister is replaced with a solid metal surface 420 to prevent liquid cryogen draining. To accommodate low levels of liquid cryogen in a Dewar, the canister is fitted with sintered metal 320 section that acts as a permeable membrane to allow liquid cryogen to slowly fill over several hours. The speed of the cryogen moving through the sintered metal section can be modified depending on the embodiment based on factors including the type of cryogen, the permeability of the sintered metal section, and the size of the sintered metal section within the solid metal surface making up the bottom of the container.

FIG. 4C depicts aspects of Design 2. This canister is lined with a liquid cryogen absorbent material 325 to both provide thermal insulation from the environment and blanket semen straws with cold cryogen vapor as the liquid vaporizes. In some embodiments, the absorbent material is a material that absorbs liquid nitrogen. In some embodiments, the absorbent material is a felted material, such as fabricated from cotton or polyester. In some embodiments, the absorbent material is an acrylic felt material. In some embodiments, the absorbent material is a fiberglass mesh or weave material. In some embodiments, the absorbent material is an aerogel material. In some embodiments, the absorbent material is a cryogel material. In some embodiments, the absorbent material is a cryogen-permeable material with porosity. The absorbent material can be, for example, between approximately 2 mm in thickness and approximately 7 mm in thickness, depending on the material used. The absorbent material can be, for example, approximately 2 mm in thickness. The absorbent material can be, for example, approximately 3 mm in thickness. The absorbent material can be, for example, approximately 4 mm in thickness. The absorbent material can be, for example, approximately 5 mm in thickness. The absorbent material can be, for example, approximately 6 mm in thickness. The absorbent material can be, for example, approximately 7 mm in thickness.

A grated metal surface 430 is included as a permeable layer and positioned to protect the liquid cryogen absorbent material within the wall of the container. The grated metal surface is fabricated from a material that is thermally conductive at cryogenic temperatures, for example stainless steel or copper. The grated metal surface is sufficiently thermally conductive to equalize the temperature along the interior surface of the container when the container is removed from liquid cryogen within a Dewar for semen straw removal. The grated metal surface equalizes the temperature quickly, within seconds, and maintains the equalized temperature during the period that the container is raised above the liquid cryogen. The grated metal surface includes a plurality of holes positioned and angled to direct cryogen vapor into the interior of the container and to surround any portion of semen straws within the container above the liquid cryogen with cryogen vapor for maintenance of a temperature close to that of the liquid cryogen during a straw removal. Some embodiments include the absorbent material and the grated metal surface along the walls and the bottom of the container. Some embodiments include the absorbent material and the grated metal surface along the walls only, and not along the bottom of the container. The grated metal surface connects at the top edge with an angled connection to the outer wall of the container, the angled connection also thermally conductive to equalize heat throughout the length of the container interior from the top edge to the bottom.

FIG. 4D depicts aspects of Design 3. A solid cylinder 340 is designed to fit snugly within the canister to increase thermal mass. In some embodiments, the solid cylinder is aluminum. A system of holes 335 is drilled along its length to accommodate semen straws. The holes 335 can be sized and positioned to contain semen straws in an easy position for handling and/or organization during storage.

In the first approach (Design 1) we sought to maintain a level of liquid cryogen within the canister by replacing the grate at the canister base with a solid metal surface 420 (see FIG. 4B). We designed a canister that possesses drain holes 400 drilled along the circumference of the canister approximately half way (e.g. 5 cm) from its bottom to allow liquid cryogen to flow between the canister and the Dewar. In addition, the drain holes allow the canister to gradually sink when it is inserted into the Dewar. A vapor guard 310 is positioned adjacent to the drain holes 400, the vapor guard 310 affixed to the interior of the canister wall 315 at a position above the drain holes 400. This prototype is similar to several existing canisters with the notable difference that our design allows for significantly higher levels of liquid cryogen in the canister.

The intention of the features of Design 1 was to drive cold cryogen vapor over the top portion of the straws that are not submerged in liquid cryogen. However, when we removed our canister prototype from the Dewar neck, we noticed that a significant portion of cryogen vapor escapes from the drain holes. To minimize this effect we modified the design to include a vapor guard on the inside wall of the canister along the circumference that covers the drain holes and extends below the liquid cryogen level (see FIG. 4B).

To accommodate low levels of liquid cryogen in a Dewar we fitted the canister with sintered metal 320 within the base that acts as a permeable membrane to allow liquid cryogen to slowly fill over several hours while restricting the loss of liquid cryogen during a straw extraction event lasting up to a few minutes (see FIG. 4B). The sintered metal permits some passage of the liquid cryogen but this occurs slowly enough so that the liquid cryogen is maintained within the canister during a relatively brief raising of the canister above the liquid nitrogen, for example during straw extraction. The sintered metal does, however, permit the container to gradually refill with liquid cryogen when the container is repositioned within the liquid cryogen for storage. The use of this prototype extends the effectiveness of this device when the liquid cryogen level in the Dewar drops below the elevation of the drain holes.

In the second approach (Design 2) we sought to provide thermal insulation from the environment and blanket semen straws with cold cryogen vapor as liquid cryogen vaporizes. To do this, we designed a canister lined with an liquid cryogen absorbent material (see FIG. 4C). The thickness of the material was intended to store sufficient liquid cryogen for an exposure lasting several minutes. Addition of a thermally conductive grated metal surface further equalized the temperature along the length of the container when the canister is raised above the liquid cryogen. The grated metal surface acts both as a thermal conductor with the remaining liquid cryogen as a heat sink in the lower portion of the container as well as includes a plurality of holes which are positioned and angled to direct cryogen vapor into the interior of the container. The cryogen vapor is the product of the recent evaporation of the liquid cryogen, and is therefore at a temperature close to that of the liquid cryogen. This gas flow from the edges of the container into the center also minimizes gas flow into the interior of the container from the relatively warmer upper air when a container is raised for a semen straw extraction event. For canisters with a grated base, we also tested the liquid cryogen absorbent material at the canister base to allow liquid to fill and drain during use but minimize natural convection of cold vapors when the canister was raised in the Dewar.

In the final approach (Design 3) we sought to increase thermal mass of the canister to slow the temperature rise during an exposure (see FIG. 4D). We machined a solid aluminum cylinder 340 to fit snugly within the canister and drilled a system of holes 335 along its length to accommodate several semen straws. This prototype increases organization within the canister and allows straws from different bulls to be separated in different regions within a canister in a similar manner to how goblets function in larger Dewars.

In some embodiments, a canister for liquid cryogen storage includes: a cylindrical cup with a circular side wall and a bottom wall; a series of apertures in the circular side wall; and a flange affixed to an interior surface of the circular side wall at a position adjacent to the apertures. In some embodiments, the cylindrical cup includes: a cylindrical cup of a size and shape to fit through the neck of a Dewar and to be retained within the inner storage region of the Dewar. In some embodiments, the cylindrical cup includes: a cylindrical cup of a size and shape to retain a plurality of bovine semen straws.

In some embodiments, a canister for liquid cryogen storage includes a series of apertures in a circular side wall, wherein the series of apertures are positioned around the circular side wall at positions approximately midway between the bottom edge and the top edge of the side wall. In some embodiments, a canister for liquid cryogen storage includes a series of apertures in a circular side wall, wherein the series of apertures are positioned around the circular side wall at positions approximately one third of the distance from the bottom edge relative to the top edge of the side wall. In some embodiments, a canister for liquid cryogen storage includes a series of apertures in a circular side wall, wherein the series of apertures are positioned around the circular side wall at positions between approximately midway between the bottom edge and the top edge of the side wall and approximately one third of the distance from the bottom edge relative to the top edge of the side wall.

In some embodiments, a canister for liquid cryogen storage includes a flange affixed to an interior surface of the circular side wall at a position adjacent to the apertures, and wherein the flange affixed to an interior surface of the circular side wall is positioned to substantially cover the series of apertures in the circular side wall. In some embodiments, a canister for liquid cryogen storage includes a flange affixed to an interior surface of the circular side wall at a position adjacent to the apertures, and wherein the flange affixed to an interior surface of the circular side wall is positioned to partially cover the series of apertures in the circular side wall. In some embodiments, a canister for liquid cryogen storage includes a flange affixed to an interior surface of the circular side wall at a position adjacent to the apertures, and wherein the flange affixed to an interior surface of the circular side wall is affixed to the interior surface of the circular side wall at a position above the series of apertures.

In some embodiments, a canister for liquid cryogen storage further includes a permeable membrane positioned within the bottom wall. The permeable membrane can include, for example, a sintered metal. The permeable membrane can include, for example, a membrane permeable to liquid nitrogen. The permeable membrane can, for example, be permeable to liquid nitrogen at a rate sufficient to allow the cylindrical cup to fill in an hour when the cylindrical cup is submerged in liquid nitrogen. The permeable membrane can, for example, be permeable to liquid nitrogen at a rate sufficient to allow the cylindrical cup to fill in a period longer than a minute when the cylindrical cup is submerged in liquid nitrogen. In some embodiments, a canister for liquid cryogen storage further includes a handle affixed to the canister.

In some embodiments, a canister for liquid cryogen storage includes: a cylindrical cup with a circular side wall and a bottom wall; and a layer of absorbent material affixed to the interior surface of the circular side wall, the absorbent material absorbent to a liquid cryogen. In some embodiments, the cylindrical cup includes: a cylindrical cup of a size and shape to fit through the neck of a Dewar and to be retained within the inner storage region of the Dewar. In some embodiments, the cylindrical cup includes: a cylindrical cup of a size and shape to retain a plurality of bovine semen straws.

In some embodiments, a canister for liquid cryogen storage includes a layer of absorbent material affixed to an interior surface of a circular side wall, the absorbent material absorbent to a liquid cryogen. The absorbent material can, for example, include a material that absorbs liquid nitrogen. The absorbent material can, for example, include a felted material. The absorbent material can, for example, include a fiberglass mesh material. The absorbent material can, for example, include an aerogel material. The absorbent material can, for example, include a cryogen-permeable material with porosity.

In some embodiments, a canister for liquid cryogen storage further includes a cryogen-permeable region within the bottom wall. The cryogen-permeable region within the bottom wall can include, for example, a group of apertures within the bottom wall. The cryogen-permeable region within the bottom wall can include, for example, a sintered metal. The cryogen-permeable region within the bottom wall can include, for example, a group of apertures within the bottom wall.

In some embodiments, a canister for liquid cryogen storage further includes a permeable layer positioned adjacent to the layer of absorbent material at a surface of the layer of absorbent material opposite to the canister. The permeable layer can include, for example, a layer of metal including a plurality of apertures. In some embodiments, a canister for liquid cryogen storage further includes a layer of absorbent material affixed to the interior surface of the bottom wall. In some embodiments, a canister for liquid cryogen storage further includes a handle affixed to the canister.

In some embodiments, a canister for liquid cryogen storage includes: a cylindrical cup with a circular side wall and a bottom wall; and a solid mass of a size and shape to substantially fill the interior of the cylindrical cup, the solid mass including a plurality of cavities positioned vertically in the solid mass. In some embodiments, the cylindrical cup includes: a cylindrical cup of a size and shape to fit through the neck of a Dewar and to be retained within the inner storage region of the Dewar. In some embodiments, the cylindrical cup includes: a cylindrical cup of a size and shape to retain a plurality of bovine semen straws.

In some embodiments, a canister for liquid cryogen storage includes a cylindrical cup with a circular side wall and a bottom wall, and wherein the cylindrical cup includes a cryogen-permeable region within the bottom wall. In some embodiments, the cryogen-permeable region within the bottom wall includes a group of apertures in the bottom wall.

In some embodiments, a canister for liquid cryogen storage includes a solid mass of a size and shape to substantially fill the interior of the cylindrical cup, the solid mass including a plurality of cavities positioned vertically in the solid mass. In some embodiments, the solid mass is a thermal mass. In some embodiments, the solid mass is fabricated with metal. The plurality of cavities positioned vertically in the solid mass can include, for example, a plurality of cavities of a size and shape to contain one or more semen straws. The plurality of cavities can be, for example, positioned so that a user of the container can quickly identify and remove particular semen straws. In some embodiments, a canister for liquid cryogen storage further includes a handle affixed to the canister.

Results—Protection of Semen from Damage

Since Prototype 2, based on Design 2, demonstrated improvement in maintaining temperature and reducing the loss of LN during testing, we tested its ability to protect against semen damage in comparison to the standard canister. Both a standard canister and Prototype 2, based on Design 2, were subjected to multiple ambient temperature exposures similar to those described herein. Semen stored in the Prototype 2 canister showed less damage by post-thaw acrosome integrity measurements (see FIGS. 12A & 12B). These data strongly suggest that a canister lined with an LN absorbent material can better maintain the fertility of frozen semen when subjected to repeated poor handling.

Herein we show that damage associated with improper access of cryogenically stored bovine semen is mitigated with simple and inexpensive improvements to the storage system. An alternative solution to this problem is to train AI technicians and semen handlers to avoid exposing frozen semen straws to non-LN temperatures for more than a few seconds. While proper technique is stressed in many training programs, the problem of exposure-induced damage persists and is suspected to be more severe in the developing world.

It is likely that the majority of semen damage caused during improper frozen semen access is inadvertent. Inadequately trained users might assume that exposing frozen semen to ambient conditions is not damaging as long as the contents remains in a frozen state. However, thermal damage can occur after very brief ambient exposures that are not sufficient to thaw the semen.

Studies suggest that damage due to brief ambient exposures results when the bulk product temperature rises above $-137°$ C. (Debenedetti, P. G. Supercooled and glassy water, *J. Phys.-Condes. Matter* 15, R1669-R1726 (2003), which is incorporated herein by reference)—the glass transition temperature of water—and then cools back down when reintroduced to LN (Stroud, B., Consequences of mishandling frozen semen and embryos in *Proceedings, Applied Reproductive Strategies in Beef Cattle—Northwest* 191-204 (2012) and Berndtson, W. E., Pickett, B. W., Rugg, C. D. & Collins, F. Procedures for Field Handling of Bovine Semen in Plastic Straws, 51-60 (1976), which are each incorporated by reference). The reordering of water molecules during these events likely affects multiple aspects of semen biology associated with fertilizing potential. While these insults are presumably stochastics, they appear to have a greater chance of negatively affecting the integrity of biological membranes since we observed damage via the acrosomal assay but not the motility or viability assays. The exact mechanism of this phenomenon has yet to be fully elucidated, but it may share similarities to cryocapacitation, a form of cryoinjury that can occur during the freezing process that largely affects sperm outer and acrosomal membranes (Bailey, J., Bilodeau, J. & Cormier, N., Semen cryopreservation in domestic animals: A damaging and capacitating phenomenon minireview, *J. Androl.* 21, (2000) and Partyka, A., Niżański, W. & Ochota, M. in *Current Frontiers in Cryobiology* (ed. Katkov, I. I.) 547-575 (InTech, 2012). doi:10.5772/1962, which are each incorporated by reference).

In this study we exposed frozen bovine semen to poor practices that mimic improper access, and subsequently measured semen damage. The relationship between exposure time and acrosome damage is complex but our data are consistent with the hypothesis that damage accumulates upon fluctuations about the glass and freezing transitions. To decrease thermal fluctuations within the canister contents, we designed several simple and inexpensive improvements to the Dewar canister. These improvements, such as canisters lined with an LN absorbent material, better maintain characteristics of semen that are associated with fertilizing potential.

We hesitate to extrapolate the effect that this technological mitigation would have on actual fertilization rates. Poor handling is one of several factors that affect AI success and poor handling behaviors occur with variable frequencies and severities, making it difficult to quantify their full effect. Furthermore, we constrained our evaluation to a select number of aspects of sperm biology that are necessary for fertilization (Ikawa, M., Inoue, N., Benham, A. M. & Okabe, M. Fertilization: A sperm's journey to and interaction with the oocyte, *J. Clin. Invest.* 120, 984-994 (2010), which is incorporated herein by reference). Of the biological aspects we investigated, we suspect that the assays do not fully reflect damage that poor handling imparts. For example, the results from the acrosomal integrity assay are reliant on gross morphological differences in these structures. We suspect that this assay underestimates the level of acrosomal damage by failing to register submicroscopic injuries that negatively affect fertility.

Since all current in vitro semen assays suffer from some degree of sensitivity limitations and because each assay measures only a subset of aspects needed for a semen straw to result in heifer fertilization—including in vitro fertilization (Ball, G. D. et al. Factors affecting successful in vitro fertilization of bovine follicular oocytes, *Biol. Reprod.* 28, 717-725 (1983), which is incorporated by reference herein)—predicting the fertilizing potential of a semen straw in a laboratory setting is a dubious exercise (Rodriguez,-Martinez, H. Can We Increase the Estimative Value of Semen Assessment. *Reproduction Domest. Anim.* 41, 2-10 (2006); Oliveira, L. Z., Monteiro, F. M., Carla, E. & Celeghini, C. *Success in Artificial Insemination—Quality of Semen and Diagnostics Employed. inntech open* (2013) and Rodriguez-Martinez, H., Laboratory Semen Assessment and Prediction of Fertility: still Utopia?, *Reprod. Domest. Anim.* 38, 312-318 (2003), which are each incorporated by reference herein). While we are reluctant to quantify the impact of our Dewar improvements without a full-fledged field study, our results imply it will lead to higher rates of AI success.

The intention of this study was to find technological solutions that would lead to a higher AI success rate—and therefore higher farmer incomes—in the developing world. Of course, any technological solution will need to pass several hurdles, in addition to such a technical evaluation, for it to result in this goal. Among these challenges are those associated with any requirements on the user to interact with the equipment differently than they currently do.

In a field observation we sought feedback regarding prototypes based on all three designs. Our assessment of the improved canisters was carried out in Kenya where we conducted 17 one-on-one interviews, mock insemination workstations with AI technicians, and 30 interviews in group settings that included seventeen practicing AI technicians, four semen distributers, two senior AI educators and seven leaders, managers and policy directors in the dairy sector in Kenya. All observations and interviews found no observable difference in how the prototype canisters were handled or managed as compared to standard equipment (data not shown).

Among the learnings from this evaluation was the observation that AI technicians in rural Kenya invariably operate with partially filled LN Dewars. To ensure that the performance of the prototypes mentioned herein do not suffer as a result of this behavior (intended to save on LN costs), we repeated thermal performance and acrosomal integrity assays with partially filled Dewars. Results from these studies suggest that the protection that the Prototype 2 canister imparts is minimally affected by the amount of LN in the Dewar (see FIGS. 11D and 12B).

Our findings are applicable to industries outside of the AI industry as well. Maintenance of the cold chain is crucial to preserve the integrity of a variety of biological samples such as seeds, oocytes, blood products, embryos, stem cells, and tissues from humans, animals and plants (Hubel, A., Spindler, R. & Skubitz, A. P. N., Storage of human biospecimens: selection of the optimal storage temperature. *Biopreserv. Biobank.* 12, 165-75 (2014), which is incorporated herein by reference). Inventory control methods such as those described here could limit thermal fluctuations within these samples and protect them from cryodamage. These technologies may be especially useful for samples frozen using vitrification, a process often used in the preservation of oocytes, embryos, and stem cells, which leaves the samples especially sensitive to devitrification damage (Sansinena, M., Santos, M. V., Taminelli, G. & Zaritky, N., Implications of storage and handling conditions on glass transition and potential devitrification of oocytes and embryos, *Theriogenology* 82, 373-378 (2014), which is incorporated herein by reference).

In some embodiments, a canister for liquid cryogen storage includes: a cylindrical cup with a circular side wall and a bottom wall; a layer of absorbent material positioned adjacent to the interior surface of the circular side wall, the absorbent material absorbent to a liquid cryogen; a layer of thermally conductive material adjacent to the layer of absorbent material, the layer of thermally conductive material including a plurality of holes; and a connection between a top edge of the thermally conductive material and a top edge of the circular side wall.

Figure 14:
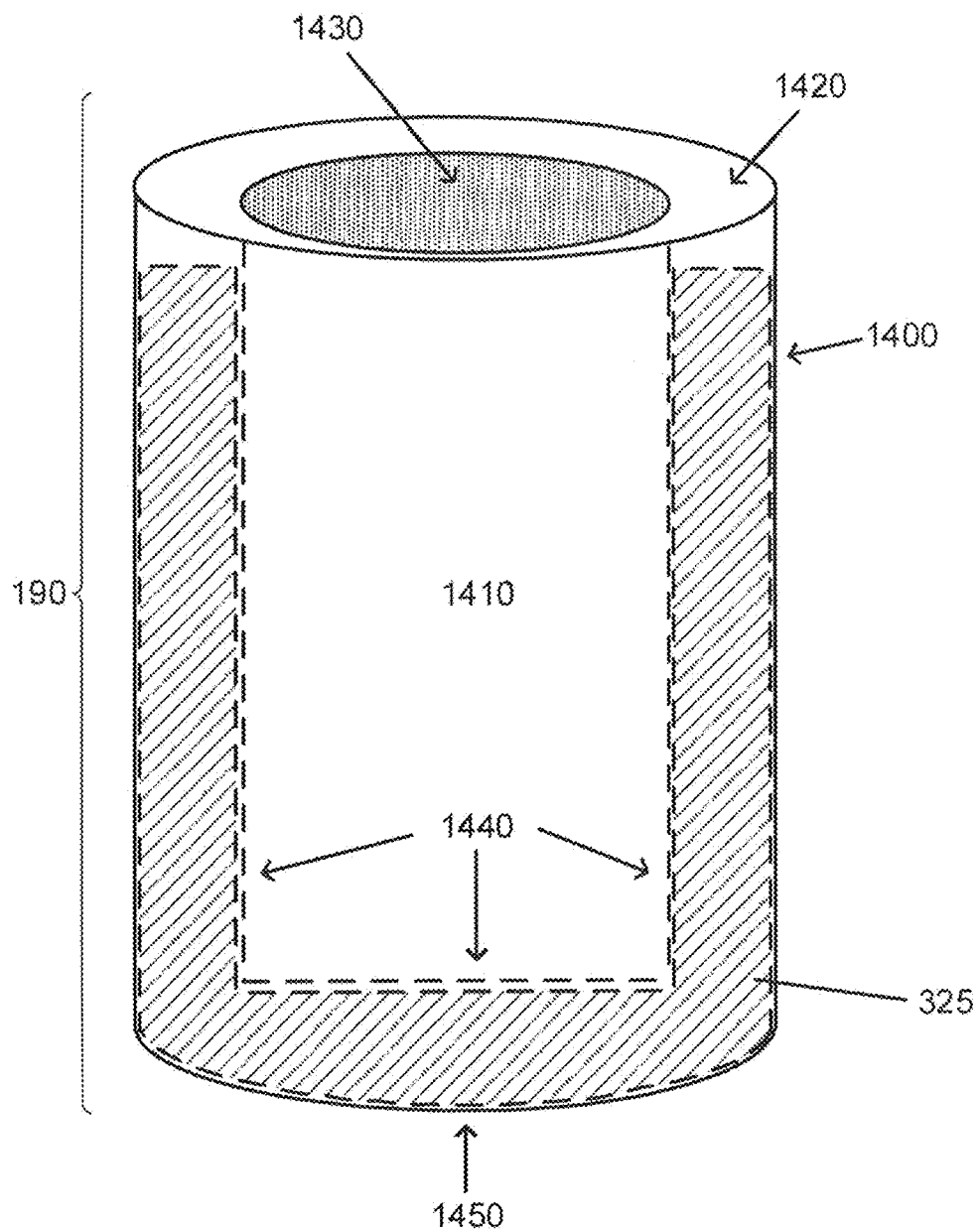
FIG. 14 depicts aspects of a canister.

FIG. 14 depicts aspects of a canister embodiment of Design 2, above. The canister is shaped as a right circular cylinder. The canister includes a container 190 in the shape of a cylindrical cup with a circular side wall 1400 and a bottom wall 1450. The container 190 includes an aperture 1430 at the top, the aperture of a size and shape to accept the insertion and removal of standard-sized semen straws. The interior 1410 of the container 190 is of a size and shape to retain and store a plurality of standard-sized semen straws. A handle is connected to the canister, the handle positioned for raising and lowering the canister during storage while minimizing the time involved in handling the canister as well as the potential hazard to a user of materials held at liquid cryogen temperatures. The cylindrical cup is fabricated from a thermally conductive material which is durable in the temperature range of the liquid cryogen that the container will be submerged in during use.

In some embodiments, the cylindrical cup includes a circular side wall containing a plurality of apertures between one third to one half the distance from the bottom wall to the top edge of the circular side wall. The apertures are sized and positioned to permit liquid cryogen to enter the interior of the container when the container is partially submerged in a liquid cryogen. In some embodiments, the cylindrical cup includes a circular side wall that is solid.

In some embodiments, the cylindrical cup includes a bottom wall that contains a plurality of apertures. In some embodiments, the cylindrical cup includes a bottom wall that is solid. In some embodiments, the cylindrical cup includes a bottom wall that includes a sintered metal section, the section configured to permit a reduced flow of liquid cryogen into and out of the interior of the container. In some embodiments, the cylindrical cup includes a cryogen-permeable region within the bottom wall. The cryogen-permeable region can include a sintered metal. The cryogen-permeable region can include a group of apertures within the bottom wall.

The container 190 includes a layer of absorbent material 325 positioned adjacent to the interior surface of the circular side wall 1400, the absorbent material absorbent to a liquid cryogen. In some embodiments, the liquid cryogen expected to be used with the container is liquid nitrogen and the absorbent material is absorbent to liquid nitrogen. In some embodiments, the layer of absorbent material is a felted material. In some embodiments, the layer of absorbent material is a fiberglass mesh material. In some embodiments, the layer of absorbent material is an aerogel material. In some embodiments, the layer of absorbent material is a cryogen-permeable material with porosity. In some embodiments, the layer of absorbent material is positioned only adjacent to the circular side wall of the container, extending from the bottom to the top of the container. In some embodiments, the layer of absorbent material is further positioned adjacent to the interior surface of the bottom wall.

The container 190 also includes a layer of thermally conductive material 1440 adjacent to the layer of absorbent material 325. The layer of thermally conductive material 1440 includes a plurality of holes in the material, the holes sized, shaped, oriented and positioned to direct cryogen vapor from the layer of absorbent material 325 into the interior 1410 of the container 190. The holes are sized, shaped, oriented and positioned to direct the cryogen vapor from evaporated liquid cryogen within the layer of absorbent material radially into the center of the container interior. During use, this just-evaporated cryogen vapor is only a few degrees above the temperature of the liquid cryogen, and therefore the vapor flow maintains a near-liquid cryogen temperature for semen straws within the container when the container is raised from the liquid cryogen bath. The expanding vapor within the container interior also creates a gas flow up through the top aperture of the container, reducing the entrance of potentially warmer air from an exterior of the container when the container is raised. For example warmer air may enter a Dewar when the lid is removed, and this warmer air may be adjacent to the aperture of a container when it is raised within the Dewar as shown in FIGS. 2B and 2C.

In some embodiments, the layer of thermally conductive material is a material thermally conductive at a boil point of the liquid cryogen. For example the material can be stainless steel for use with liquid nitrogen as a liquid cryogen. In some embodiments, the layer of thermally conductive material includes a plurality of holes sized and positioned to direct cryogen vapor through the layer of thermally conductive material and into the interior of the container. For example the holes may be positioned radially around the layer of thermally conductive material. For example the holes may be oriented to direct the cryogen vapor across the layer of thermally conductive material at an angle substantially parallel to the plane formed by the bottom wall of the container. For example the holes may be oriented along azimuth and directed radially toward a center axis of the container. For example the holes may be sized to permit a volume of cryogen vapor per unit time into the interior of the container, the volume and unit of time depending on the liquid cryogen and the expected use of an embodiment.

The container 190 includes a connection 1420 between a top edge of the layer of thermally conductive material and a top edge of the circular side wall 1400. In some embodiments, the connection 1420 is continuous with the layer of thermally conductive material 1440 and affixed at the top edge to the circular side wall 1400 of the cylindrical cup. The connection 1420 is in thermal contact with both the top edge of the layer of thermally conductive material 1440 and a top edge of the circular side wall 1400. For example in some embodiments the connection 1420, the layer of thermally conductive material 1440 and the circular side wall 1400 are fabricated from a contiguous piece of thermally conductive metal, such as stainless steel or copper. For example in some embodiments the connection 1420, the layer of thermally conductive material 1440 and the circular side wall 1400 are fabricated from different pieces of thermally conductive metal that are connected together with thermally conductive attachments during manufacture. The connection 1420 can be angled relative to the planes of the layer of thermally conductive material 1440 and the circular side wall 1400 as well as the plane of the bottom wall 1450. The angle of the connection 1420 can be positioned and oriented to provide convenient access to standard sized semen straws stored within the interior 1410 to a user moving quickly to access the stored straws and return the unused ones to storage. The connection can be solid, without apertures, which maintains the cryogen vapor at a level below the lower edge of the connection and in a level within the container to escape through the plurality of holes in the layer of thermally conductive material.

In some embodiments, the connection is fabricated from a material thermally conductive at a boil point of the liquid cryogen. For example if the liquid cryogen used with an embodiment is liquid nitrogen, the connection can be fabricated from stainless steel. The connection can include a surface facing the aperture of the container which is sufficiently smooth to not hinder a semen straw being slide along the surface when being added or removed from the interior of the container. For example if the connection is fabricated from stainless steel, the stainless steel can be polished or otherwise made sufficiently smooth.

In some embodiments, a container includes a bottom layer of thermally conductive material including a plurality of holes positioned adjacent to the bottom wall, the bottom layer of thermally conductive material affixed to the layer of thermally conductive material along the side walls. In some embodiments, a container includes a layer of absorbent material positioned adjacent to the interior surface of the bottom wall as well as a bottom layer of thermally conductive material including a plurality of holes positioned adjacent to the bottom wall, the bottom layer of thermally conductive material affixed to the layer of thermally conductive material along the side walls.

EXAMPLES

Reagents

Unless otherwise indicated, reagents used in this study were purchased from Sigma (St. Louise, Mo.). All frozen semen used in the study was purchased from Accelerated Genetics (Baraboo, Wis.). Unless otherwise indicated, semen within an experiment utilized straws from a single lot, which in some tests were from the Holstein Bull Michigan Frost (014HO07313) and packaged in 0.5 ml French straws.

Example 1: Quantifying Semen Damage

Figure 5:
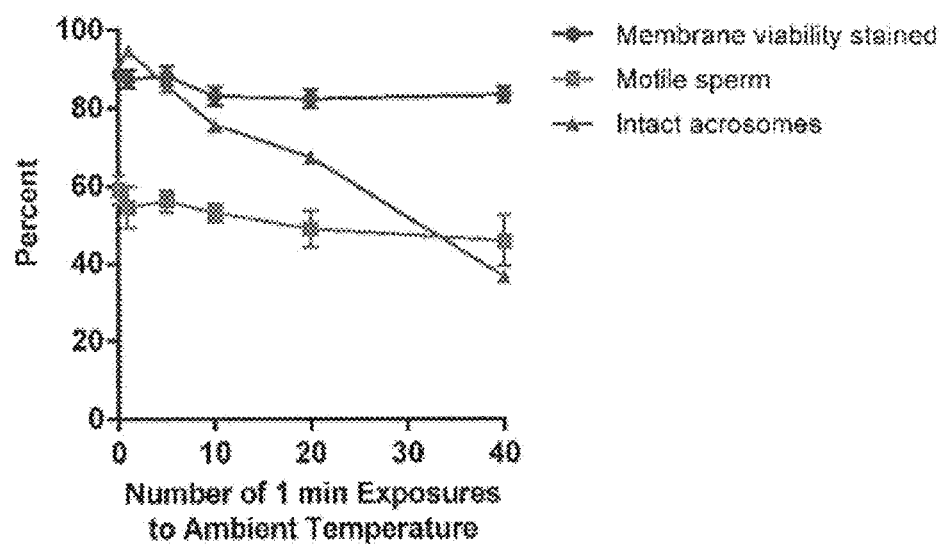
FIG. 5 is a graph depicting test results.

FIG. 5 depicts post-thaw characteristics of frozen semen subjected to repeated ambient temperature exposures. Frozen straws from the same lot of semen were stored in the canister of a standard 3 L Dewar and subjected to repeated one minute ambient temperature exposures. Measurements of membrane viability staining, sperm motility, and acrosome integrity are displayed in FIG. 5. Membrane viability and sperm motility data points were measured on three samples. Error bars represent standard deviation (SD). Each acrosome integrity data point was measured on samples from a single straw. Error bars are not included on the acrosome integrity data set.

To quantify the damage associated with these types of repeated exposures, we subjected the goblet of a standard 3 L Dewar containing frozen semen to recurring ambient temperature exposures (23° C.±1° C.) and repeated these treatments at various exposure durations. Between each exposure, the canister was submerged in a LN-filled Dewar for at least one minute. After these cycling treatments were complete, we measured aspects of semen biology that correlate with fertility (H. Rodriguez,-Martinez, "Can We Increase the Estimative Value of Semen Assessment," Reproduction Domest. Anim., Vol. 41, pp. 2-10, 2006 and L. Z. Oliveira, F. M. Monteiro, E. Carla, and C. Celeghini, Success in Artificial Insemination—Quality of Semen and Diagnostics Employed. 2013, which are each incorporated by reference).

Figure 6:
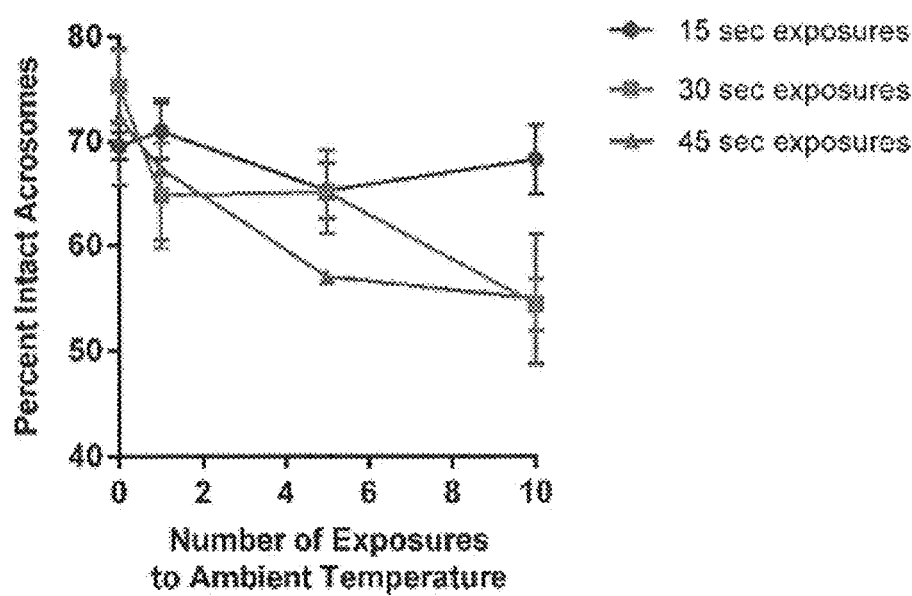
FIG. 6 is a graph depicting test results.

Both semen motility and outer membrane viability staining were resistant to these treatments (see FIG. 6). A relatively large number of one minute exposures were required to induce measureable damage in these physiological characteristics.

However, damage to the acrosome was much more pronounced (see FIGS. 5 and 6). The acrosome is a large vesicle located at the anterior region of the sperm head that contains hydrolytic enzymes and surface antigens necessary for the acrosome reaction, a necessary process in fertilization, where the sperm penetrates the zona pellucida of the egg (M. Ikawa, N. Inoue, A. M. Benham, and M. Okabe, "Fertilization: A sperm's journey to and interaction with the oocyte," J. Clin. Invest., Vol. 120, No. 4, pp. 984-994, 2010 which is incorporated by reference).

Measurements showed direct relationships between acrosome damage and exposure cycle number and duration (see FIG. 6). These data are consistent with reports that show that these structures are particularly sensitive and dynamic (J. Bailey, J. Bilodeau, and N. Cormier, "Semen cryopreservation in domestic animals: A damaging and capacitating phenomenon minireview," J. Androl., Vol. 21, No. 1, 2000 which is incorporated by reference).

Example 2: Quantifying Semen Damage

Generally, Dewar canisters contain multiple semen straws. If an AI technician uses poor handling practices then each time he or she removes a straw for use, the remaining straws within the inventory will experience multiple thermal exposures (see, e.g. FIG. 2). Similar events could occur during the transfer of straws between Dewars, such as when importers transfer straws to distribution centers, distributers transfer straws to AI technicians, etc.

To quantify the damage associated with repeated thermal exposures, we subjected the canister of a standard 3 L Dewar containing frozen bovine semen to recurrent ambient temperature exposures. We repeated these cycling treatments at various exposure durations, and between each exposure the canister was submerged in LN. After cycling treatments were complete, we measured aspects of semen biology that correlate with fertility (Rodriguez,-Martinez, H. Can We Increase the Estimative Value of Semen Assessment, *Reproduction Domest. Anim.* 41, 2-10 (2006) and Oliveira, L. Z., Monteiro, F. M., Carla, E. & Celeghini, C., *Success in Artificial Insemination—Quality of Semen and Diagnostics Employed. inntech open* (2013), which are each incorporated by reference). Both semen motility and viability measurements were resistant to these treatments (see FIG. 2A). Surprisingly, 20 one minute ambient exposures were not sufficient to induce measureable damage in these physiological characteristics.

Figure 7:
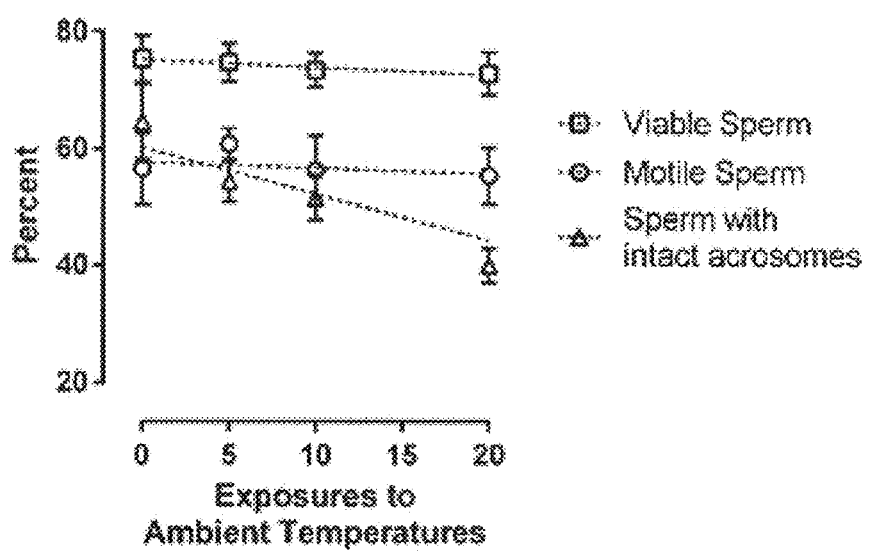
FIG. 7 is a graph depicting test results.

However, damage to the acrosome was much more pronounced (see FIG. 7). The acrosome is a large vesicle located at the anterior region of the sperm head that contains hydrolytic enzymes and surface antigens necessary for the acrosome reaction, a necessary process in fertilization where the sperm penetrates the zona pellucida of the egg (Ikawa, M., Inoue, N., Benham, A. M. & Okabe, M. Fertilization: A sperm's journey to and interaction with the oocyte, *J. Clin. Invest.* 120, 984-994 (2010), which is incorporated herein by reference). Measurements showed that acrosome damage increased with the quantity and duration of thermal exposure (see FIG. 8). These data are consistent with reports that show that acrosomes are dynamic structures particularly sensitive to damage (Bailey, J., Bilodeau, J. & Cormier, N., Semen cryopreservation in domestic animals: A damaging and capacitating phenomenon minireview, *J. Androl.* 21, (2000) and Stroud, B. Consequences of Handling Frozen Semen and Embryos. in *Proceedings, Applied reproductive strategies in Beef Cattle,* 191-204 (2012), which are each incorporated herein by reference).

Figure 8:
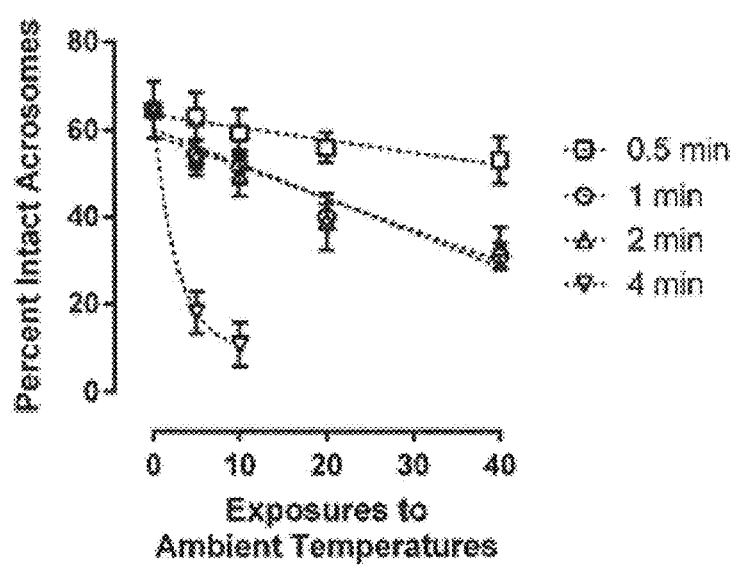
FIG. 8 is a graph depicting test results.

FIGS. 7 and 8 show that poor handling damages semen. For the data shown in FIG. 7, frozen semen straws were subjected to repeated one minute ambient temperature exposures. Measurements of membrane viability staining, sperm motility, and acrosome integrity are displayed. For the data shown in FIG. 8, frozen semen was subjected to multiple ambient temperature exposures at 0.5, 1, 2, and 4 minute durations. The post-thaw acrosome integrity measurements are shown. For both graphs, the fitted lines are included as visual guides (n=6, error bars represent standard deviation (SD)).

Example 3: Motility and Membrane Viability Staining

Frozen semen straws were thawed in a water bath set at 35° C. for 30 seconds. Motility and membrane viability staining was performed using computer assisted semen analysis (CASA). Briefly, for motility staining, 20 µL of semen was gently mixed with 30 µL Easybuffer B (IMV Technologies, Maple Grove Minn.) and 50 µL of 1 mg/ml Hoechst 33342. Samples were then incubated at 35° C. for 20 minutes, loaded onto prewarmed four chamber Leja slides (IMV Technologies) and imaged using the Animal Motility package on an IVOS II (Hamilton Thorne, Beverly, Mass.) system using version 1.5 of the CASA II sperm analysis software and the manufacturer's recommended settings.

For membrane viability staining, semen was thawed as previously described. 20 µL of semen was gently mixed with 30 µL Easybuffer B (IMV Technologies) and 50 µL of 1 mg/ml Hoechst 33258. Samples were then incubated at 35° C. for 2 minutes, loaded onto prewarmed four chamber Leja slides and imaged using the Animal Motility Viadent package on the same IVOS II system and software.

Example 4: Acrosome Integrity

Acrosome integrity measurements were adapted from previously described methods (see: E. C. C. Celeghini, R. P. De Arruda, a. F. C. De Andrade, J. Nascimento, and C. F. Raphael, "Practical techniques for bovine sperm simultaneous fluorimetric assessment of plasma, acrosomal and mitochondrial membranes," Reprod. Domest. Anim., Vol. 42, No. 5, pp. 479-488, 2007; and J. K. Graham, "Assessment of sperm quality: A flow cytometric approach," Anim. Reprod. Sci., Vol. 68, No. 3-4, pp. 239-247, 2001, which are each incorporated herein by reference.) Frozen semen straws were thawed in a water bath set at 35° C. for 30 seconds. Semen was then transferred to 1.7 mL microcentrifuge tube and incubated at 35° C. for one hour.

In some instances, samples were then cooled to 4° C. and centrifuged 500 RCF for 5 minutes at 4° C. Supernatants were then discarded and the pellet was gently resuspended in 1 mL PBS supplemented with 10% bovine serum albumin (BSA) and 25 µg/mL fluorescein conjugated peanut agglutinin (PNA-FITC). Samples were incubated for 30 minutes at 4° C. Samples were washed with PBS supplemented with 10% BSA, resuspended in 0.5 mL Cytofix (BD Biosciences, Franklin Lakes, N.J.), and incubated for 15 minutes at 4° C. Samples were then centrifuged 500 RCF for 5 minutes at 4° C., and the pellets were resuspended in PBS supplemented with 10% BSA. 20 µL of this suspension was spread on a microscope slide and mixed with a drop of Fluoroshield with DAPI mounting medium. Acrosome integrity was measured using fluorescence microscopy as previously described (E. C. C. Celeghini, R. P. De Arruda, a. F. C. De Andrade, J. Nascimento, and C. F. Raphael, "Practical techniques for bovine sperm simultaneous fluorimetric assessment of plasma, acrosomal and mitochondrial membranes," Reprod. Domest. Anim., Vol. 42, No. 5, pp. 479-488, 2007, which is incorporated by reference).

In some instances, after the semen was transferred to 1.7 mL microcentrifuge tube and incubated at 35° C. for one hour, 20 µL of semen solution was spread on a microscope slides and air-dried for 15 min. The slides were fixed by immersion in absolute methanol for 15 min. Slides were rinsed in PBS baths twice for 5 min each, transferred to a bath containing 25 µg/mL PNA-FITC for 30 min, and rinsed in three PBS baths for five minutes each. Slides were gently dried using compressed air. One drop of Fluoroshield™ with DAPI Histology Mounting Medium was then applied to each slide and acrosome integrity was measured using fluorescence microscopy as previously described (Celeghini, E. C. C., De Arruda, R. P., De Andrade, a. F. C., Nascimento, J. & Raphael, C. F. Practical techniques for bovine sperm simultaneous fluorimetric assessment of plasma, acrosomal and mitochondrial membranes, *Reprod. Domest. Anim.* 42, 479-488 (2007); P. Lybaert, A. Danguy, F. Leleux et al., Improved methodology for the detection and quantification of the acrosome reaction in mouse spermatozoa, Histol Histopathol (2009) 24: 999-1007; S. Esteves, R. Sharma, A. Thomas, A. Agarwal. Evaluation of Acrosomal Status and Sperm Viability in Fresh and Cyropreserved Specimens by the Use of Fluorescent Peanut Agglutinin Lectin in conjunction with Hyo-osmotic Swelling Test. International Braz J Urol, 33 (3): 364-376, 2007; and Carrel, Aston Eds. Spermatogenesis: Methods and Protocols, Methods in Molecular Biology, Vol. 927 (2013) which are each incorporated herein by reference).

Example 5: Instrumented Semen Straw

A bundle of three 36 AWG Type T thermocouples was inserted into a semen straw. The thermocouple tips were positioned 34 mm, 79 mm, and 124 mm from the crimped end of the straw. The bundle was secured to the crimped end of the straw using 19 mm Kapton tape, waxed lacing cord, and tapered round rubber plugs.

Each thermocouple was connected to a National Instruments data acquisition system with a Labview interface and sampled at 1 Hz. All thermocouples were two-point-calibrated using a water bath and LN bath.

Example 6: Prototypes

Prototypes based of all three designs were constructed and subjected to ambient exposure tests described below. In this study the holes on the Design 1 prototype were located at the canister midpoint. A vapor guard and permeable membrane are not included in this data set. The Design 2 prototype used a standard canister fitted snuggly with a 9.5 mm thick cabosil infused blanket against the base and walls. LN was able to drain out when raised from the Dewar. The Design 3 prototype fitted an aluminum block with twenty 3.2 mm thru holes into a standard canister.

Standard canisters of a YDS-3 Dewar (Chart, Garfield Heights, Ohio) were used as the platform for prototype construction. The canister for Prototype 1 was modified by welding a circular piece of sheet metal to seal the canister bottom and drilling 3.175 mm diameter holes at the canister midpoint. A custom aluminum ring, 2.1 mm thick, was designed to fit snuggly on the inside of the canister, 5 mm above the holes at the midpoint extending 12 mm downward (see FIGS. 3B and 4B). A 1.25 mm gap allowed the LN to flow through the holes at the midpoint.

Prototype 2 was fitted snuggly with a 5 mm thick Cryogel® (Aspen Aerogels, Northborough, Mass.) blanket against the base and walls.

Prototype 3 fitted an aluminum block with eight 7.2 mm thru holes into a standard canister.

Figure 10:
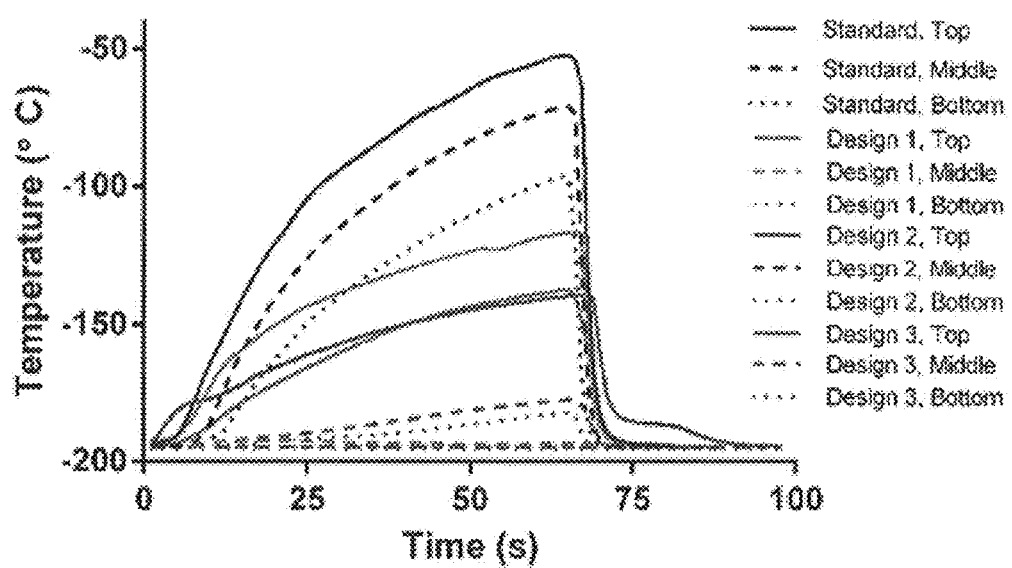
FIG. 10 is a graph depicting test results.

Each test was carried out by placing three straws instrumented with thermocouples in a canister. Each instrumented straw had three 36 gauge type T thermocouples that were positioned at the bottom, middle, and top of the straw. Each canister was raised by hand out of the Dewar into the environment and held for approximately one minute then re-submerged into the Dewar. FIG. 10 compares the thermal response of each design with the standard canister as a baseline. All three designs demonstrate an improvement delaying a temperature rise in the straws. Of note all three prototypes are very effective at keeping the mid and lower portion of the straw near the LN temperature. Designs 2 and 3 appear to be slightly more effective at delaying the temperature rise in the top portion of the straw. Additional experiments are planned to confirm this finding. The subject experiment was performed in a laboratory held at 23° C.±0.2° C. throughout the experiment. The effect of convection from small oscillations while holding the canister and cross flow from the air handling system were not measured. However, thermal response simulations using Comsol, a multiphysics modeling and simulation tool, suggest that natural convection is a driving factor and likely marginalizes potential forced convection effects in our laboratory experiment. Further testing is planned to quantify the effect of wind and direct solar radiation on the prototypes' thermal response.

Figure 9:
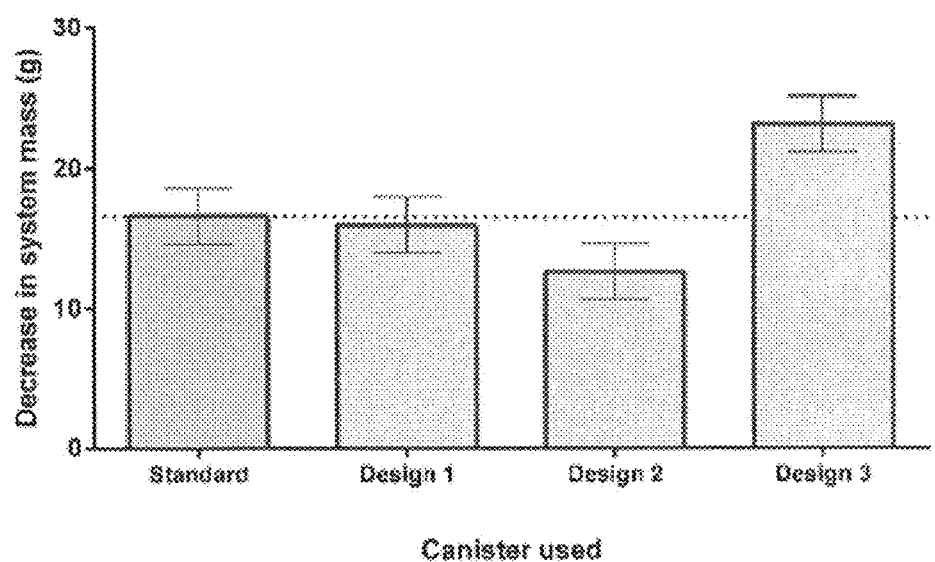
FIG. 9 is a graph depicting test results.

Testing to compare LN loss by cycling the canisters was also carried out by measuring the change in mass of the entire system, i.e. the Dewar and canister (see FIG. 9). As a reference the standard canister loses approximately 16 g of LN which is similar to the Design 1 prototype. The Design 2 prototype loses approximately 13 g, a slight improvement on the standard canister while Design 3 consumes slightly more LN. Mass loss is averaged over three trials with all data within ±2 g of the respective mean. We note that the LN mass loss for a given design is a combination of LN that evaporates when the canister is exposed to the environment and from the boiling that occurs when the canister is re-inserted into the Dewar.

FIG. 9 is a comparison of LN loss after poor handling. Canisters were removed from a full 3 L Dewar for one minute then reintroduced to the system. The loss in mass is shown (n=3, error bars represent SD). FIG. 10 shows a graph of temperature as a function of time for straws in the Design 1, 2, and 3 prototypes removed from LN in a 3 L Dewar to ambient temperature for approximately 1 min after which time, canisters are re-submerged into LN. The standard canister is shown for reference.

Example 7: Thermal Performance

We subjected the prototypes to ambient exposure tests by placing thermocouple temperature sensors at the top, middle, and bottom of a semen straw. Each prototype contained three straws with thermocouples. We raised the canister prototypes completely out of a LN-filled Dewar for approximately one minute then re-submerged into the Dewar. The experiment was performed in a laboratory held at 23° C.±0.2° C. throughout the experiment.

Figure 11:
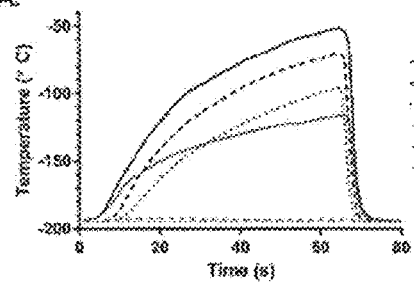
FIG. 11A is a graph depicting test results.
FIG. 11B is a graph depicting test results.
FIG. 11C is a graph depicting test results.
FIG. 11D is a graph depicting test results.
Figure 11:
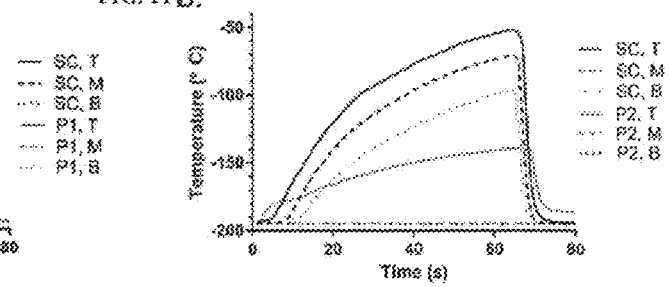
Figure 11:
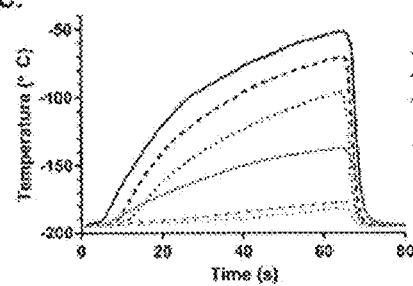
Figure 11:
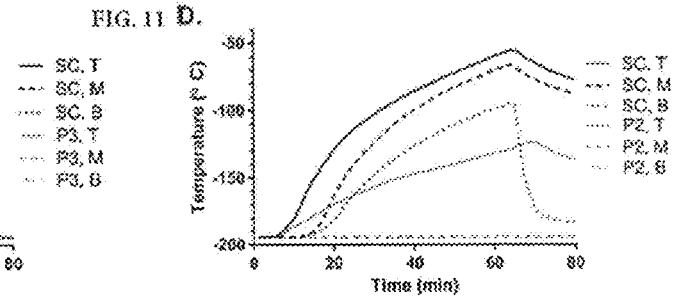

FIG. 11 shows that prototypes reduce thermal fluctuations within semen straws during poor handling. Temperature measurements at the top (T), middle (M), and bottom (B) of a semen straw placed within Prototype (P) 1 representing Design 1, Prototype 2 representing Design 2 and Prototype 3 representing Design 3 (subfigures A, B, and C, respectively) removed from a full 3 L Dewar for approximately one minute then re-submerged into LN are shown. Readings from similar experiments using a standard canister (SC) are shown for reference. D. The experiment in subfigure B was repeated with a Dewar that was 25% full of LN. All plots report values as mean readings from thermocouples located on three different semen straws from the same ambient exposure. Data are representative of three independent experiments.

All three prototypes demonstrated an improvement in delaying a temperature rise in the straws (see FIG. 11). The three prototypes effectively maintained the mid and lower portion of the straw near the −196° C. LN temperature. Prototypes 2 and 3 were slightly more effective at retaining the temperature in the top portion of the straw. The effect of convection from small oscillations while holding the canister and cross flow from the air handling system were not measured. However, thermal response simulations using a multiphysics modeling and simulation tool (COMSOL, Stockholm, Sweden) suggest that natural convection is a driving factor and likely marginalizes potential forced convection effects in this experiment (data not shown).

FIG. 11 is a set of graphs of testing results indicating that prototypes reduce thermal fluctuations within semen straws during poor handling. Temperature measurements at the top (T), middle (M), and bottom (B) of a semen straw placed within Design (P) 1, 2 and 3 (subfigures A, B, and C, respectively) removed from a full 3 L Dewar for approximately one minute then re-submerged into LN are shown. Readings from similar experiments using a standard canister (SC) are shown for reference.

FIG. 11D. The experiment in subfigure 11B was repeated with a Dewar that was 25% full of LN. All plots report values as mean readings from thermocouples located on three different semen straws from the same ambient exposure. Data are representative of three independent experiments.

To compare LN loss due to cycling the canisters, we measured the change in mass of the entire system, i.e. the Dewar and canister (see FIG. 9). The standard canister results in the loss of approximately 16 g of LN; we observed a similar loss with the Prototype 1. Prototype 2 lost approximately 13 g, a slight improvement on the standard canister, while Prototype 3 consumed more LN at 21.3 g. We note that the LN mass loss for a given prototype was a combination of LN that evaporated when the canister was exposed to the environment and from the boiling that occurred when the canister was re-inserted into the Dewar.

Example 8: Validation

The ability of the Design 1 prototype to protect against semen damage was tested in a side-by-side experiment with a standard canister. A Design 1 prototype, with holes located at the midline without the vapor guard and permeable membrane, and a standard canister both containing frozen semen from three different bulls were subjected to multiple ambient temperature exposures similar to those previously described. Post-thaw acrosome integrity analysis showed greater damage in the semen from all three bulls when the standard canister was used. These data suggest that an improved canister can better maintain the fertility of frozen semen when subjected to poor handling (see FIG. 13).

FIG. 9 illustrates mass of liquid nitrogen loss after a canister was removed from a 3 L Dewar for one minute then reintroduced to the system.

At the time of this of submission, experiments to further compare the effects of repeated thermal exposures on frozen semen stored in the prototype canisters were in progress. We intend to include these results in a future presentation.

Figure 13:
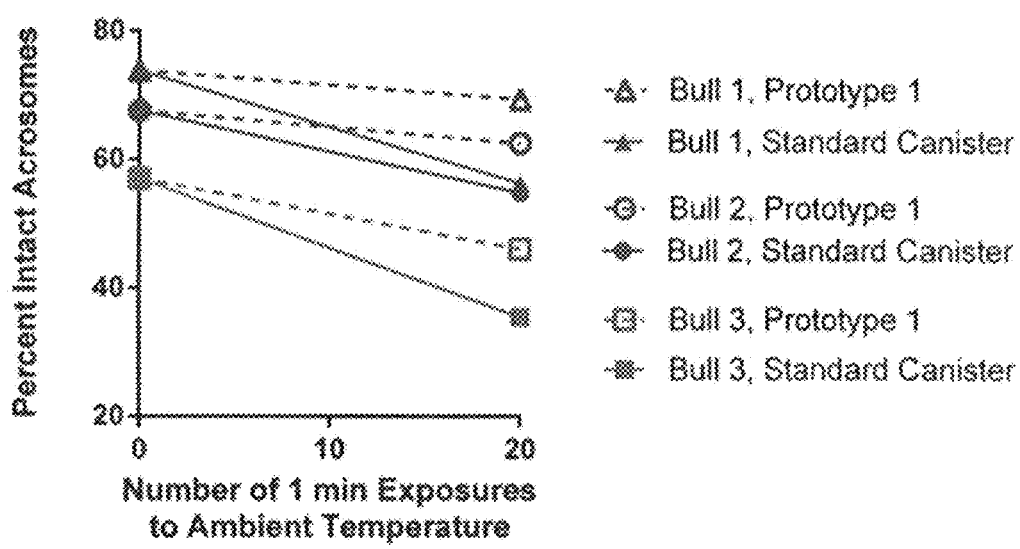
FIG. 13 is a graph depicting test results.

FIG. 13 shows post-thaw acrosome integrity measurements of frozen semen stored in the Design 1 prototype and a standard canister subjected to up to twenty 1 min ambient temperature exposures.

Example 9: Thermal Cycling Experiments

Thermal cycling experiments were performed in a laboratory with ambient conditions measuring 22±1° C. A total of six 0.5 ml semen straws occupied the canister for all exposures. For experiments utilizing a full LN Dewar, canisters were returned to the Dewar for at least one minute between exposures. For experiments utilizing a 25% LN Dewar, canisters were returned to the Dewar for at least ten minutes between exposures. Calibration experiments determined that these durations were sufficient to return the semen straw to LN temperatures.

Example 10: Protection of Semen from Damage

Figure 12A:
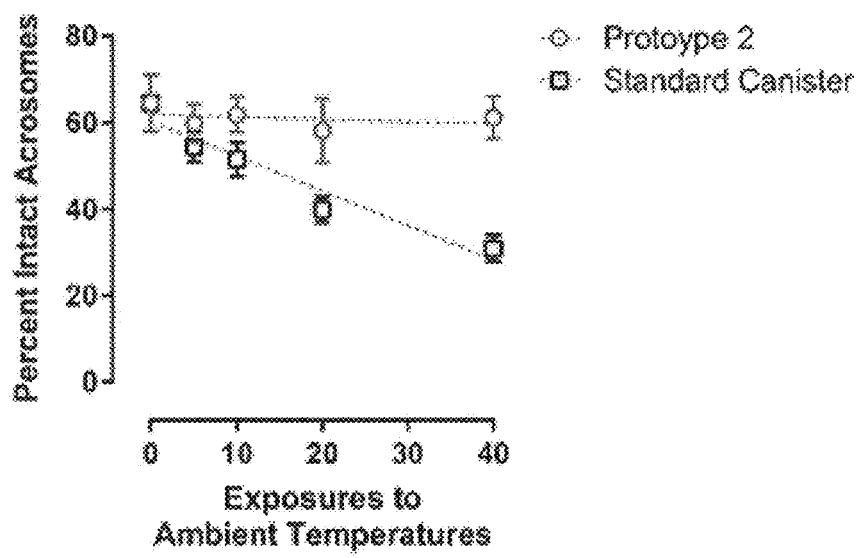
FIG. 12A is a graph depicting test results.
Figure 12B:
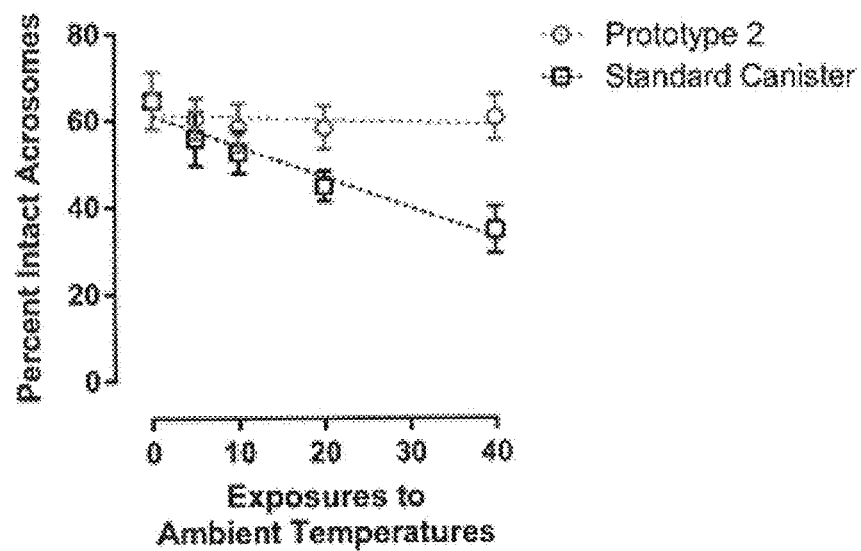
FIG. 12B is a graph depicting test results.

FIGS. 12A & 12B. Prototype 2 protects semen from poor-handling-induced damage. Frozen semen straws were placed within either a standard canister or Prototype 2 in a full (A) or 25% full (B) Dewar and exposed to up to 40 one minute ambient temperature exposures. The post thaw acrosome integrity measurements are shown. Fitted lines are included as visual guides.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A canister for liquid cryogen storage, comprising:
 a cylindrical cup with a circular side wall and a bottom wall;
 a layer of absorbent material positioned adjacent to an interior surface of the circular side wall, the absorbent material absorbent to a liquid cryogen;
 a layer of thermally conductive material adjacent to the layer of absorbent material, the layer of thermally conductive material including a plurality of holes;
 a connection between a top edge of the layer of thermally conductive material and a top edge of the circular side wall; and
 a cryogen-permeable region within the bottom wall.

2. The canister for liquid cryogen storage of claim 1, wherein the circular side wall is substantially solid.

3. The canister for liquid cryogen storage of claim 1, wherein the cylindrical cup comprises:
 the bottom wall containing a plurality of apertures.

4. The canister for liquid cryogen storage of claim 1, wherein the layer of absorbent material comprises:
 a material that absorbs liquid nitrogen.

5. The canister for liquid cryogen storage of claim 1, wherein the layer of absorbent material comprises:
 a felted material.

6. The canister for liquid cryogen storage of claim 1, wherein the layer of absorbent material comprises:
 a fiberglass mesh material.

7. The canister for liquid cryogen storage of claim 1, wherein the layer of absorbent material comprises:
 an aerogel material.

8. The canister for liquid cryogen storage of claim 1, wherein the layer of absorbent material comprises:
 a cryogen-permeable material with porosity.

9. The canister for liquid cryogen storage of claim 1, wherein the layer of thermally conductive material comprises:
 a material thermally conductive at a boil point of the liquid cryogen.

10. The canister for liquid cryogen storage of claim 1, wherein the layer of thermally conductive material is sized and positioned to direct cryogen vapor through the layer of thermally conductive material and into an interior of the container.

11. The canister for liquid cryogen storage of claim 1, wherein the layer of thermally conductive material is sized and positioned along the circular side wall from a position adjacent to the bottom wall of the cylindrical cup to a position adjacent to the connection.

12. The canister for liquid cryogen storage of claim 1, wherein the connection comprises:
 a material thermally conductive at a boil point of the liquid cryogen.

13. The canister for liquid cryogen storage of claim 1, wherein the connection is continuous with the layer of thermally conductive material and affixed at the top edge of the thermally conductive material to the circular side wall of the cylindrical cup.

14. The canister for liquid cryogen storage of claim 1, wherein the cryogen-permeable region within the bottom wall includes a sintered metal.

15. The canister for liquid cryogen storage of claim 1, wherein the cryogen-permeable region within the bottom wall includes a group of apertures within the bottom wall.

16. The canister for liquid cryogen storage of claim 1, further comprising:
 a layer of absorbent material positioned adjacent to the interior surface of the bottom wall.

17. The canister for liquid cryogen storage of claim 1, further comprising:
 a bottom layer of thermally conductive material including a plurality of holes positioned adjacent to the bottom wall, the bottom layer of thermally conductive material affixed to the layer of thermally conductive material along the side walls.

18. The canister for liquid cryogen storage of claim 1, further comprising:
 a handle affixed to the canister.

* * * * *